United States Patent
Kriheli et al.

(10) Patent No.: US 9,510,997 B2
(45) Date of Patent: Dec. 6, 2016

(54) CLOSED DRUG TRANSFER SYSTEM

(71) Applicant: EQUASHEILD MEDICAL LTD., Tefen Industrial Park (IL)

(72) Inventors: Marino Kriheli, Tel Aviv (IL); Raanan Tavor, Yuvalim (IL)

(73) Assignee: Equashield Medical Ltd., Tefen Industrial Park (IL)

( * ) Notice: Subject to any disclaimer, the term of this patent is extended or adjusted under 35 U.S.C. 154(b) by 0 days.

(21) Appl. No.: 14/762,225

(22) PCT Filed: Feb. 3, 2014

(86) PCT No.: PCT/IL2014/050112
§ 371 (c)(1),
(2) Date: Jul. 21, 2015

(87) PCT Pub. No.: WO2014/122643
PCT Pub. Date: Aug. 14, 2014

(65) Prior Publication Data
US 2015/0359709 A1    Dec. 17, 2015

(30) Foreign Application Priority Data
Feb. 7, 2013 (IL) .......................... 224630

(51) Int. Cl.
*A61J 1/20* (2006.01)
*A61M 5/162* (2006.01)

(52) U.S. Cl.
CPC .............. *A61J 1/2013* (2015.05); *A61J 1/2051* (2015.05); *A61J 1/2072* (2015.05); *A61J 1/2096* (2013.01); *A61M 5/162* (2013.01)

(58) Field of Classification Search
CPC ......... A61J 1/145; A61J 1/2096; A61J 1/2037
See application file for complete search history.

(56) References Cited

U.S. PATENT DOCUMENTS

| | | | |
|---|---|---|---|
| 2,872,494 A | 2/1959 | Rumberg et al. | |
| 4,588,403 A | 5/1986 | Weiss et al. | |
| 4,834,152 A * | 5/1989 | Howson | A61J 1/2089 141/27 |
| 5,827,262 A | 10/1998 | Neftel et al. | |
| 6,206,858 B1 | 3/2001 | Kempen et al. | |
| 8,196,614 B2 | 6/2012 | Kriheli | |

(Continued)

FOREIGN PATENT DOCUMENTS

| | | |
|---|---|---|
| WO | 84/04673 A1 | 12/1984 |
| WO | 2011104712 A1 | 9/2011 |
| WO | 2012063230 A1 | 5/2012 |

OTHER PUBLICATIONS

Corrected Version International Preliminary Report on Patentability for a counter-part application—PCT/IL2014/050112—mailed Mar. 11, 2015; 24 pages.

*Primary Examiner* — Leslie Deak
(74) *Attorney, Agent, or Firm* — Roach Brown McCarthy & Gruber, P.C.; Kevin D. McCarthy

(57) ABSTRACT

The application describes innovative designs for components of a drug transfer apparatus that overcome problems encountered in daily use of prior art apparatuses. Specifically described are components configured to prevent liquid from entering the air chamber of syringes coupled to the apparatus and to prevent tearing of the rubber stopper of drug vials when they are attached to the apparatus.

17 Claims, 36 Drawing Sheets

(56) References Cited

U.S. PATENT DOCUMENTS

2004/0211484 A1   10/2004  Fournie et al.
2005/0016626 A1    1/2005  Wilcox et al.
2010/0218846 A1*  9/2010  Kriheli ................. A61J 1/2096
                                                  141/5

* cited by examiner

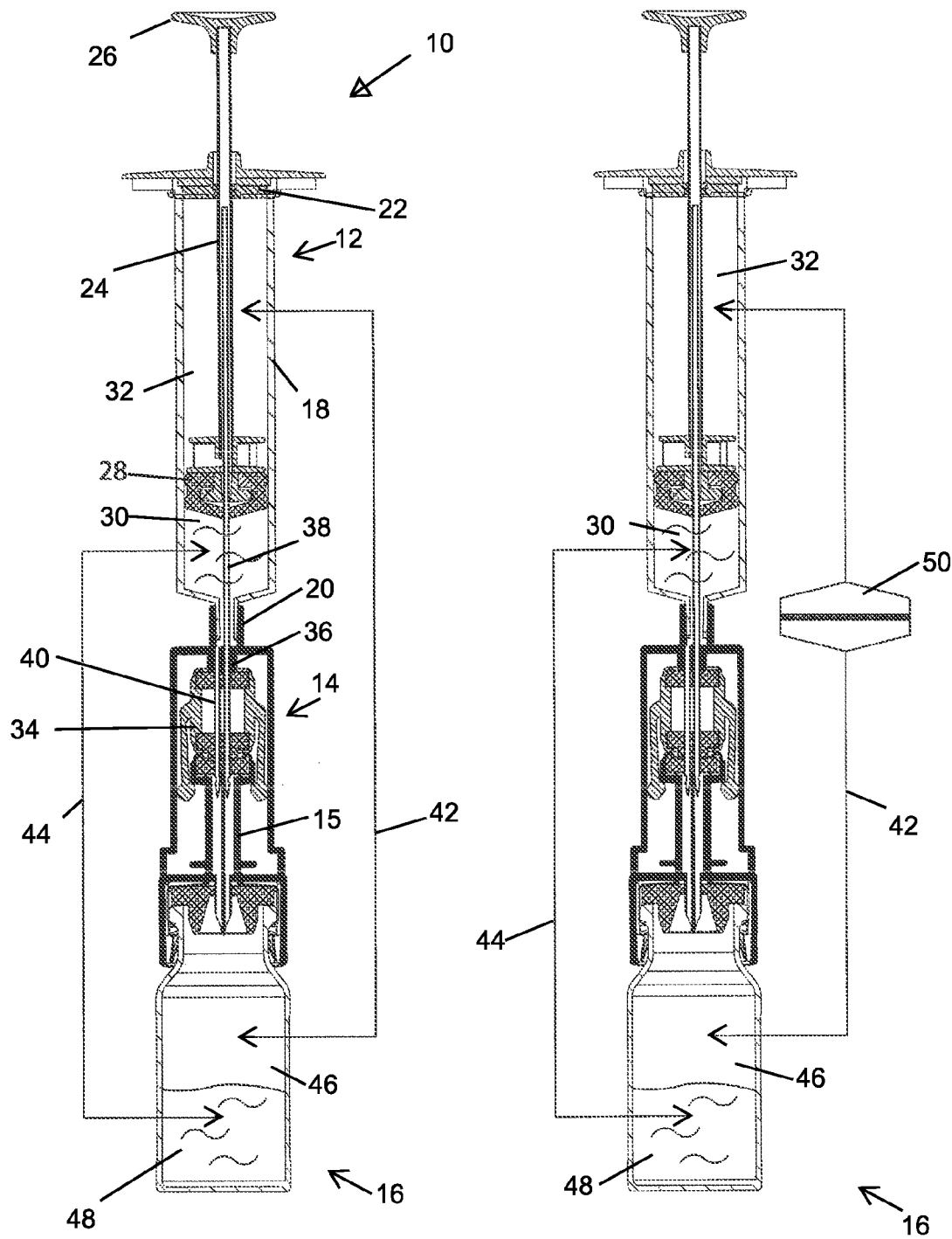

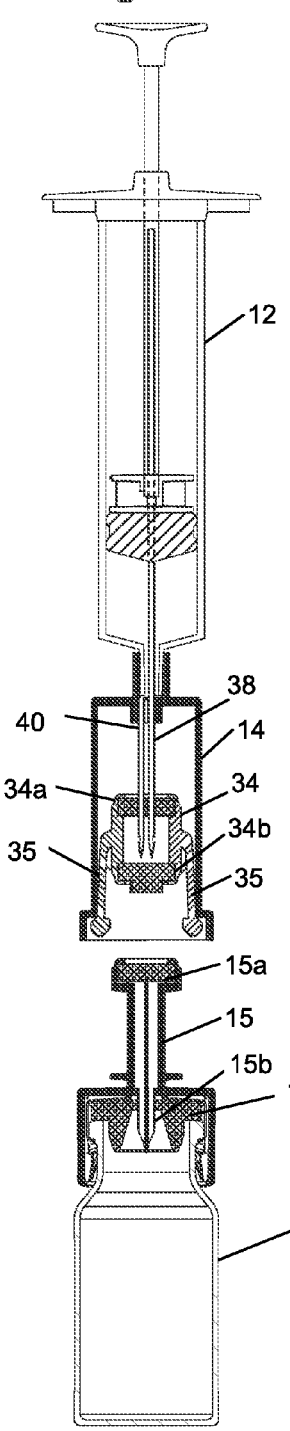
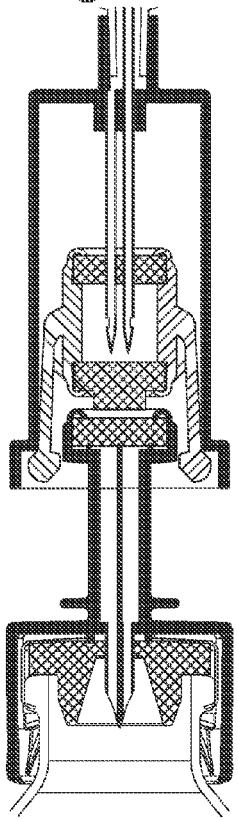
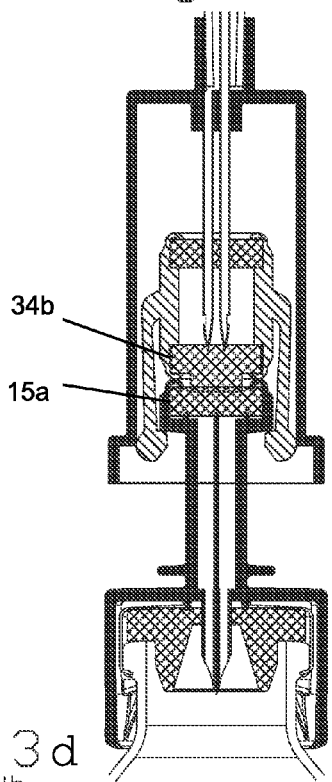
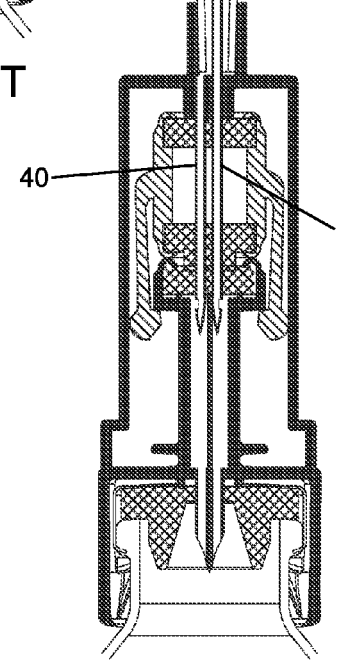
Fig. 3a
Fig. 3b PRIOR ART
Fig. 3c PRIOR ART
Fig. 3d PRIOR ART
PRIOR ART

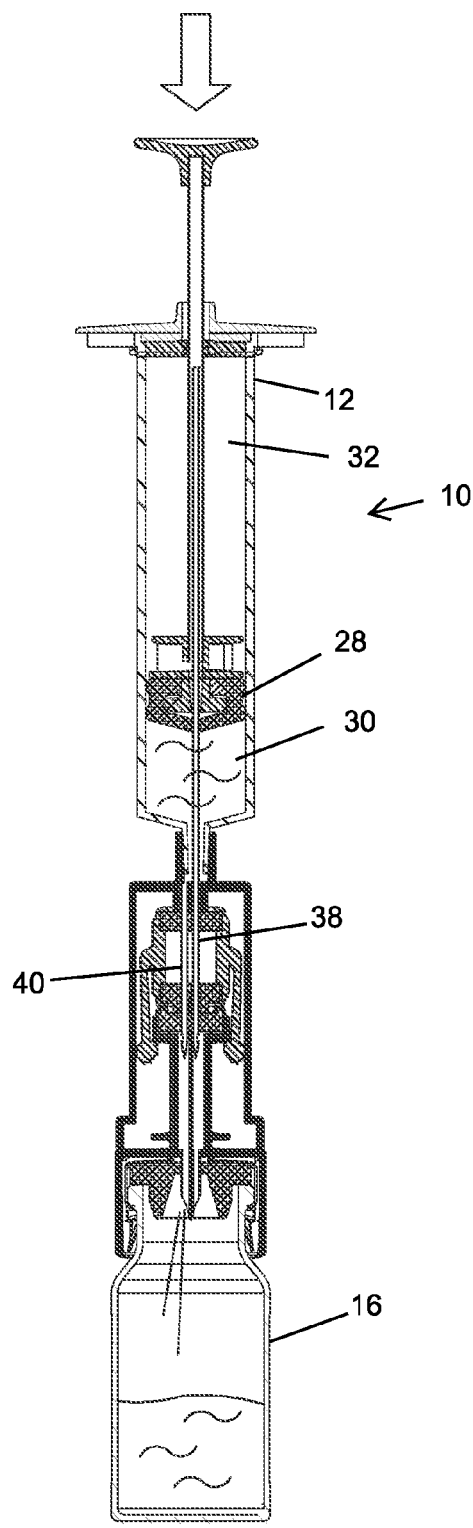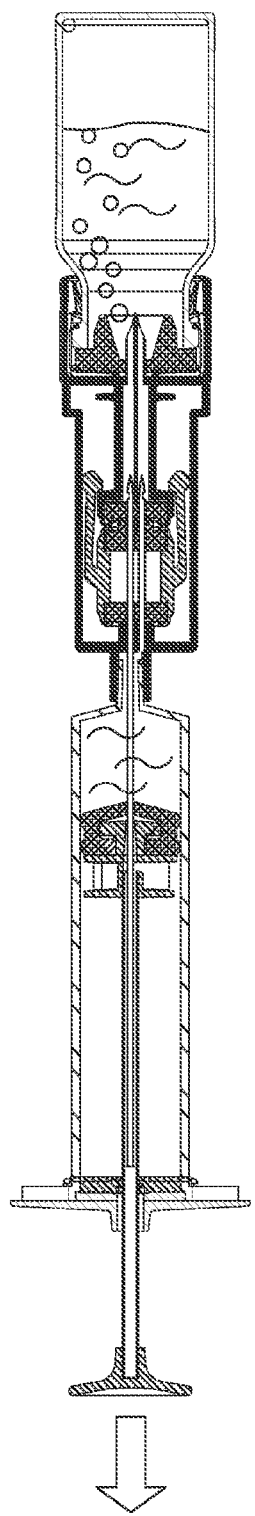

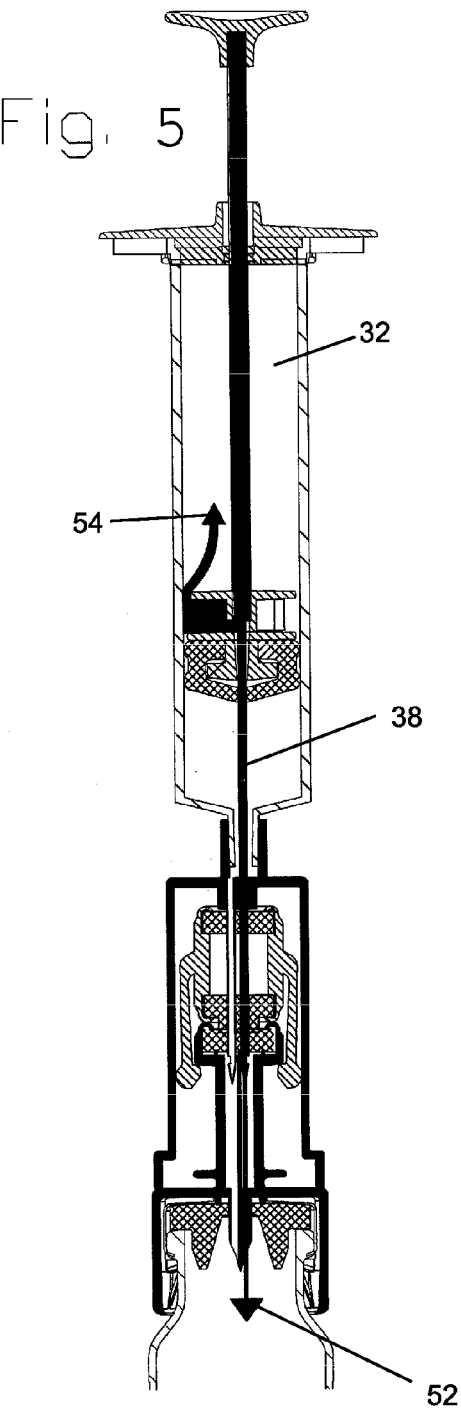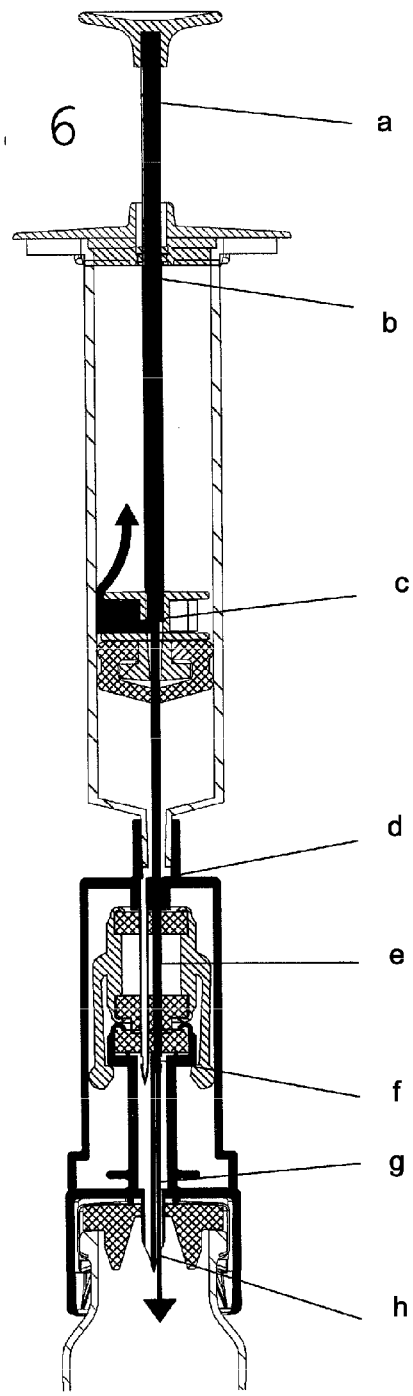
PRIOR ART

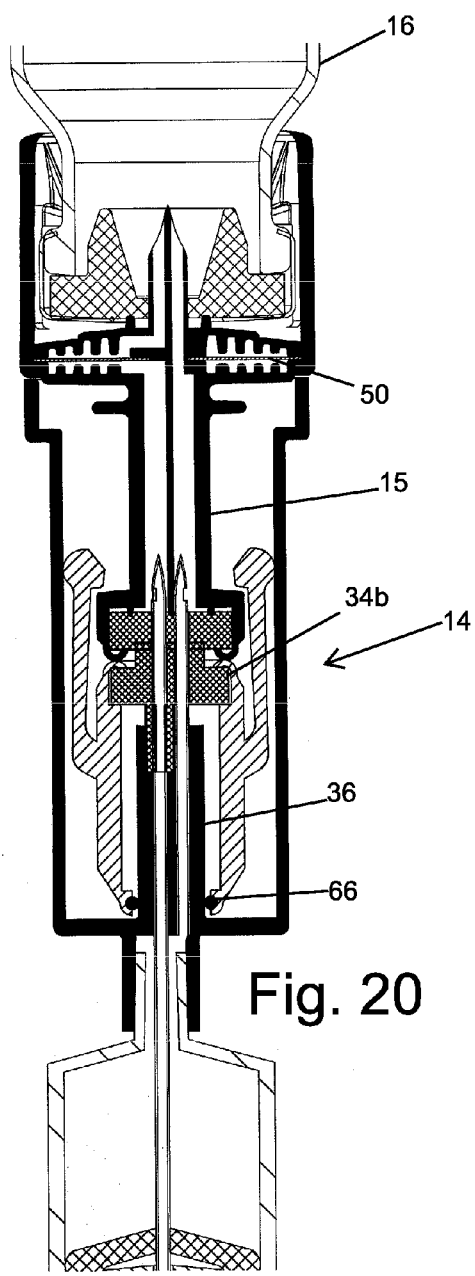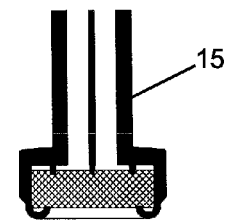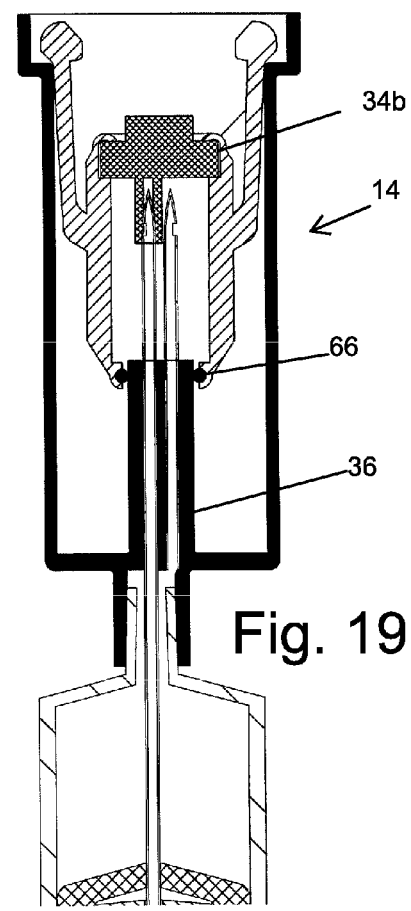
Fig. 20
Fig. 19

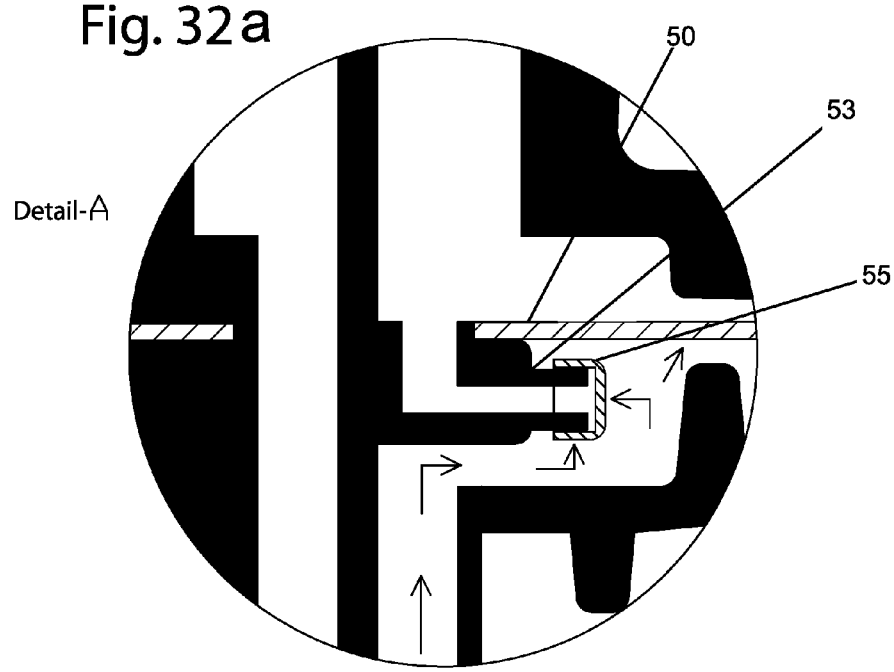
Fig. 32a
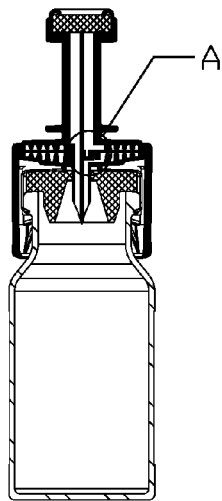
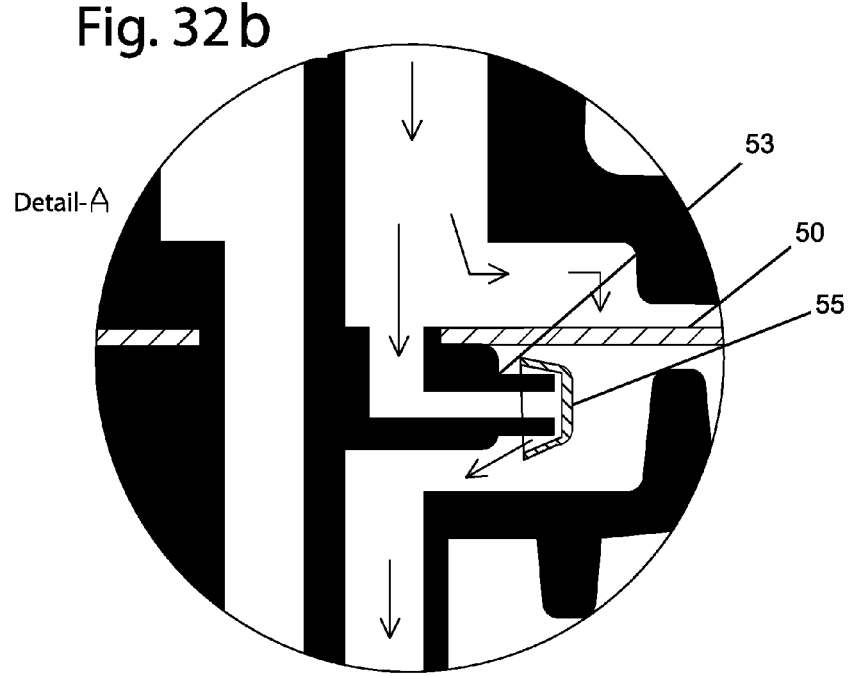
Fig. 32b

CLOSED DRUG TRANSFER SYSTEM

FIELD OF THE INVENTION

The present invention relates to the field of fluid transfer devices. More particularly, the invention relates to apparatus for the contamination-free transfer of a liquid from one container to another.

BACKGROUND OF THE INVENTION

Medical and pharmacological personnel that are involved in the preparation and administration of hazardous drugs suffer the risk of being exposed to drugs and to their vapors, which may escape to the surroundings. As referred to herein, a "hazardous drug" is any injectable material the contact with which, or with the vapors of which, may constitute a health hazard. Illustrative and non-limitative examples of such drugs include, inter alia, cytotoxins, antiviral drugs, chemotherapy drugs, antibiotics, and radiopharmaceuticals, such as herceptin, cisplatinum, fluorouracil, leucovorin, taxol, metatroxat, gemzar, cyclophosphamide, cytoxan, and neosar, or a combination thereof, in a liquid, solid, or gaseous state.

Hazardous drugs in liquid or powder form are contained within vials, and are typically prepared in a separate room by pharmacists provided with protective clothing, a mouth mask, and a laminar flow safety cabinet. A syringe provided with a cannula, i.e. a hollow needle, is used for transferring the drug from a vial. After being prepared, the hazardous drug is added to a solution contained in a bag which is intended for parenteral administration, such as a saline solution intended for intravenous administration.

Since hazardous drugs are toxic, direct bodily contact thereto, or exposure to even micro-quantities of the drug vapors, considerably increases the risk of developing health fatalities such as skin cancer, leukemia, liver damage, malformation, miscarriage and premature birth. Such exposure can take place when a drug containing receptacle, such as a vial, bottle, syringe, and intravenous bag, is subjected to overpressure, resulting in the leakage of fluid or air contaminated by the hazardous drug to the surroundings. Exposure to a hazardous drug also results from a drug solution remaining on a needle tip, on a vial or intravenous bag seal, or by the accidental puncturing of the skin by the needle tip. Additionally, through the same routes of exposure, microbial contaminants from the environment can be transferred into the drug and fluids; thus eliminating the sterility with possibly fatal consequences.

U.S. Pat. No. 8,196,614 to the inventor of the present invention describes closed system liquid transfer devices designed to provide contamination-free transfer of hazardous drugs. FIG. 1 and FIGS. 3a to 3d are schematic cross-sectional views of the apparatus 10 for transferring hazardous drugs without contaminating the surroundings, according to one embodiment of the invention described in U.S. Pat. No. 8,196,614. The main features of this apparatus that are relevant to the present invention will be described herein. Additional details can be found in the aforementioned patent.

The proximal section of apparatus 10 is a syringe 12, which is adapted to draw a desired volume of a hazardous drug from a fluid transfer component, e.g. a vial 16 or an intravenous (IV) bag in which it is contained and to subsequently transfer the drug to another fluid transfer component. At the distal end of syringe 12 is connected a connector section 14, which is in turn connected to vial 16 by means of vial adaptor 15.

Syringe 12 of apparatus 10 is comprised of a cylindrical body 18 having a tubular throat 20 that has a considerably smaller diameter than body 18, an annular rubber gasket or stopper assembly 22 fitted on the proximal end of cylindrical body 18, hollow piston rod 24 which sealingly passes through stopper 22, and proximal piston rod cap 26 by which a user can push and pull piston rod 24 up and down through stopper 22. A piston 28 made of an elastomeric material is securely attached to the distal end of piston rod 24. Cylindrical body 18 is made of a rigid material, e.g. plastic.

Piston 28, which sealingly engages the inner wall of, and is displaceable with respect to, cylindrical body 18 defines two chambers of variable volume: a distal liquid chamber 30 between the distal face of piston 28 and connector section 14 and a proximal air chamber 32 between the proximal face of piston 28 and stopper 22.

Connector section 14 is connected to the throat 20 of syringe 12 by means of a collar which proximally protrudes from the top of connector section 14 and surrounds throat 20. Note that embodiments of the apparatus do not necessarily have a throat 20. In these embodiments syringe 12 and connector section 14 are formed together as a single element at the time of manufacture, or permanently attached together, e.g. by means of glue or welding, or formed with a coupling means, such as threaded engagement or a Luer connector. The connector section 14 comprises a compressible and reciprocal double membrane seal actuator which assumes a normal, relaxed configuration in which the needles are concealed when the double membrane seal actuator is disposed in a first, distal position and which is compressed to expose the needles when proximally displaced. Connector section 14 is adapted to be releasably coupled to another fluid transfer component, which can be any fluid container with a standard connector such as a drug vial, intravenous bag, or an intravenous line to produce a "fluid transfer assembly", through which a fluid is transferred from one fluid transfer component to another.

Connector section 14 comprises a cylindrical, hollow outer body; a distal shoulder portion, which radially protrudes from the body and terminates at the distal end with an opening through which the proximal end of a fluid transfer component is inserted for coupling; a double membrane seal actuator 34, which is reciprocally displaceable within the interior of the body; and one or more resilient arms 35 serving as locking elements, which are connected at a proximal end thereof to an intermediate portion of a cylindrical actuator casing that contains double membrane seal actuator 34. Two hollow needles that function as air conduit 38 and liquid conduit 40 are fixedly retained in needle holder 36, which protrudes into the interior of connector section 14 from a central portion of the top of connector section 14.

Conduits 38 and 40 distally extend from needle holder 36, piercing the upper membrane of actuator 34. The distal ends of conduits 38 and 40 have sharp pointed ends and apertures through which air and liquid can pass into and out of the interiors of the conduits respectively as required during a fluid transfer operation. The proximal end of air conduit 38 extends within the interior of proximal air chamber 32 in syringe 12. In the embodiment shown in FIG. 1, air conduit 38 passes through piston 28 and extends inside of hollow piston rod 24. Air flowing through conduit 38 enters/exits the interior of piston rod 24 and exits/enters to air chamber 32 through an aperture formed at the distal end of piston rod 24 just above piston 28. The proximal end of liquid conduit 40 terminates at the top of or slightly proximally from the top of needle holder 36, so that the liquid conduit will be in fluid communication with the distal liquid chamber 30 via the interior of throat 20 of syringe 12.

Double membrane seal actuator 34 comprises a casing that holds a proximal disc shaped membrane 34a having a rectangular cross-section and a two level distal membrane 34b having a T-shaped cross-section with disc shaped proximal portion and a disc shaped distal portion disposed radially inwards with respect to the proximal portion. The distal portion of the distal membrane 34b protrudes distally from actuator 34. Two or more equal length resilient elongated arms 35 are attached to the distal end of the casing of actuator 34. The arms terminate with distal enlarged elements. When actuator 34 is in a first position, the pointed ends of conduits 38 and 40 are retained between the proximal and distal membranes, preventing a user from being exposed to, and injured by, the pointed ends and also isolating the ends of conduits 30 and 40 from the surroundings, thereby preventing contamination of the interior of syringe 12 and leakage of a harmful drug contained within its interior to the surroundings.

Vial adaptor 15 is an intermediate connection that is used to connect connector section 14 to a drug vial 16 or any other component having a suitably shaped and dimensioned port. Vial adaptor 15 comprises a disk shaped central piece to which a plurality of circumferential segments, formed with a convex lip on the inner face thereof for facilitating securement to a head portion of a vial 16, are attached at the circumference of the disk and pointing distally away from it and a longitudinal extension projecting proximally from the other side of the disk shaped central piece. Longitudinal extension fits into the opening at the distal end of connector section 14 to allow transfer of the drug as described hereinbelow. The longitudinal extension terminates proximally with a membrane enclosure having a diameter larger than that of the extension. A central opening in the membrane enclosure retains and makes accessible a membrane 15a.

Two longitudinal channels, which are internally formed within the longitudinal extension and that extend distally from the membrane in the membrane enclosure, are adapted to receive conduits 38 and 40, respectively. A mechanical guidance mechanism is provided to insure that the conduits 38 and 40 will always enter their designated channel within the longitudinal extension when connector section 14 is mated with vial adaptor 15. The longitudinal extension terminates distally with a spike element 15b which protrudes distally. The spike element is formed with openings in communication with the internally formed channels, respectively and openings at its distal pointed end.

Vial 16 has an enlarged circular head portion attached to the main body of the vial with a neck portion. In the center of the head portion is a proximal seal 16a, which is adapted to prevent the outward leakage of a drug contained therein. When the head portion of vial 16 is inserted into the collar portion of vial adaptor 15 and a distal force is applied to vial adaptor 15, the spike element 15b of the connector section 14 pierces the seal 16a of vial 16, to allow the internal channels in the connector section 14 to communicate with the interior of drug vial 16. When this occurs, the circumferential segments at the distal end of the collar portion of the connector section are securely engaged with the head portion of vial 16. After the seal of vial 16 is pierced it seals around the spike preventing the outward leakage of the drug from the vial. At the same time the tops of the internal channels in vial adaptor 15 are sealed by the membrane 15a at the top of vial adaptor 15, preventing air or drug from entering or exiting the interior of vial 16.

The procedure for assembling drug transfer apparatus 10 is carried out as shown in FIGS. 3a to 3d: Step 1—After the vial 16 and vial adaptor 15 have been joined together, with spike element 15b penetrating proximal seal 16a of the vial, the membrane enclosure 15a of vial adaptor 15 is positioned close to the distal opening of connector section 14, as shown in FIG. 3a. Step 2—A double membrane engagement procedure is initiated by distally displacing the body of connector section 14 with an axial motion until the membrane enclosure and longitudinal extension of vial adaptor 15 enters the opening at the distal end of the connector section 14, as shown in FIG. 3b. Step 3—the distal membrane 34b of actuator 34 is caused to contact and be pressed against the stationary membrane 15a of vial adaptor 15 by additional distal displacement of the body of the connector section 14. After the membranes are pressed tightly together the enlarged elements at the ends of the arms of the connector section 14 are squeezed into the more narrow proximal section of connector section 14 thereby holding the membranes pressed together and engaged around the longitudinal extension and under the membrane enclosure of vial adaptor 15, as shown in FIG. 3c, thereby preventing disengagement of the double membrane seal actuator 34 from vial adaptor 15. Step 4—Additional distal displacement of the body of connector section 14, as shown in FIG. 3d, causes actuator 34 to move proximally relative to the body of the connector section 15 until the tips of conduits 38 and 40 pierce the distal membrane of actuator 34 and the membrane at the top of vial adaptor 15 and are in fluid communication with the interior of vial 16. These four steps are performed by one continuous axial motion as connector section 14 is distally displaced relative to the vial adaptor 15, and they will be reversed to separate connector section 14 from vial adaptor 15 by holding connector section 14 stationary and displacing vial adaptor 15 distally. It is important to emphasize that the procedure is described herein as comprising four separate steps, however this is for ease in describing the procedure only. It is to be realized that in actual practice the secured double membrane engagement (and disengagement) procedure using the present invention is carried out using a single smooth axial movement.

After drug transfer assembly 10 shown in FIG. 1 is assembled as described hereinabove with reference to FIGS. 3a to 3d, the piston rod 24 can be moved to withdraw liquid from vial 16 or to inject liquid from the syringe into the vial. The transfer of liquid between the distal liquid chamber 30 in the syringe 12 and liquid 48 in the vial 16 and transfer of air between the proximal air chamber 32 in the syringe 12 and air 46 in the vial 16 takes place by an internal pressure equalization process in which the same volumes of air and liquid are exchanged by moving through separate channels symbolically shown in FIG. 1 by paths 42 and 44 respectively. This is a closed system which eliminates the possibility of exchange of air or liquid drops or vapor between the interior of assembly 10 and the surroundings.

FIG. 4a schematically shows injection of a liquid into a vial. To inject liquid contained in the liquid chamber 30 of syringe 12 into the vial 16 the drug transfer assembly 10 must be held vertically with the vial at the bottom in an upright position as shown in FIG. 4a. Pushing piston 28 distally pushes the liquid out of liquid chamber 30 through conduit 40 into vial 16. Simultaneously, as the volume of liquid chamber 30 is reduced by the distally moving piston, the volume of air chamber 32 is increased. This creates a temporary state of negative pressure in the air chamber and therefore air (or an inert gas) inside vial 16 will be sucked through conduit 38 into air chamber 32. Additionally and simultaneously, as the liquid is added to the vial, the volume available for the air in the vial is reduced creating a temporary state of positive pressure, therefore the air is forced from the vial 16 through conduit 38 into air chamber 32, thus equalizing the pressures in the transfer assembly 10 and equilibrium is reached when piston 28 stops moving.

FIG. 4b schematically shows withdrawal of liquid from a vial. To withdraw liquid from the vial 16 and transfer it into the liquid chamber 30 of syringe 12 the drug transfer assembly 10 must be inverted and held vertically with the vial 16 in an upside-down position as shown FIG. 4b. For this operation, when apparatus 10 is assembled and the piston 28 in syringe 12 is pulled in the proximal direction, a state of negative pressure is created in liquid chamber 30 and liquid is sucked into it through conduit 40. Simultaneously the volume of air chamber 32 is reduced and air is forced out of it through conduit 38 into the vial (in FIG. 4b are shown the air bubbles created by the air entering the vial from air chamber 40). As described in FIGS. 4a and 4b this simultaneous transfer and replacing of equal volumes of gas and liquids respectively inside syringe and vial constitutes the closed system equalization system.

Despite the care that was taken to separate air path 42 from liquid path 44 there are two locations in the prior art assembly described in U.S. Pat. No. 8,196,614 in which these paths intersect under certain conditions allowing for the possibility of liquid to travel through the air conduit from the distal liquid chamber 30 or vial 16 to the proximal air chamber.

Specifically, in the prior art apparatus described in U.S. Pat. No. 8,196,614 there is a direct connection between the air and liquid channels:

A. inside the double membrane seal actuator 34, when the syringe 12 and attached connection section 14 are not connected to any other fluid transfer component; and B. inside the vial 16 at the tip of the spike, when the apparatus 10 is assembled as shown in FIG. 1.

When part of the liquid does accidently find its way into the air chamber of the syringe, in addition to the obvious problems of esthetics, additional time consuming working steps become necessary to retrieve the drug and correct the dosage.

An example of a scenario when situation A is relevant is when the syringe contains liquid and is being handled, for example when being transported from the pharmacy to the ward. At such a time the piston rod might be accidentally pushed causing some of the drug to migrate to the proximal air chamber above the piston from where it cannot be expelled from the syringe. In such case the plunger needs to be pulled back in order to retrieve the drug, which is an extra work step and the wet residuals in the air chamber 32 cause an aesthetic problem.

An example of a scenario when situation B is relevant is when, during withdrawal of a liquid drug from a vial which is in a typical upside-down position, a bubble of air is seen to enter the liquid chamber of the syringe or when the syringe has been filled with more than the desired volume of liquid. In these situations, pushing on the piston rod to return liquid or bubble to the vial will also cause some liquid to be forced through the air channel into the air chamber in the syringe. The way to remove the bubble is a relatively time consuming and complex procedure involving disconnecting the syringe from the vial and reconnecting it. Special attention is required to avoid pushing the plunger accidentally, which slows down the speed of work.

Another difficulty with prior art drug transfer assemblies is that frequently vial adaptors are prone to leak liquid and vapor to the surroundings and, vice versa, the drug in the vial is prone to microbial contamination when air from the surroundings enters the vial due to improper attaching of the vial adaptor to the vial. When attaching vial adaptors manually, the spike is often not properly centered and/or typically is inserted into the stopper of the vial at an angle. Such inaccuracy will cause tearing of the vial rubber stopper when the vial adaptor fully settles on the vial and the locking wings enforce centered position of the spike and adaptor.

It is a purpose of the present invention to provide improvements to the previously described drug transfer devices that will prevent the above mentioned defects.

Further purposes and advantages of this invention will appear as the description proceeds.

SUMMARY OF THE INVENTION

In a first aspect the invention is a fluid transfer apparatus comprising:
(a) a syringe-like proximal section comprising:
  (i) a cylindrical body;
  (ii) a piston that is displaceable within the cylindrical body, the piston defining a distal liquid chamber and a proximal gas chamber, both of variable volume;
(b) a connector section fixedly attached to the distal end of the proximal section, wherein the distal end of the connector section is adapted to be connectable to a fluid transfer component, the connector section comprising:
  (i) a needle holder;
  (ii) a liquid conduit that passes through and is rigidly attached to the needle holder, wherein the distal end of the liquid conduit begins in the connector section and the proximal end of the liquid conduit terminates in the liquid chamber;
  (iii) an air conduit that passes through and is rigidly attached to the needle holder, wherein the distal end of the gas conduit begins in the connector section and the proximal end of the gas conduit terminates in the gas chamber; and
  (iv) a membrane located at the distal end of the connector section, wherein the membrane encloses the distal ends of the liquid conduit and the gas conduit isolating them from the surroundings.

The connector section is configured to allow a head portion of the fluid transfer component to enter the interior of the connector section and to allow the membrane in the connector section to be pushed proximally when it is contacted by a membrane located in the head portion of the fluid transfer component; whereupon further pushing of the membranes together causes the distal ends of the liquid conduit and the air conduit to penetrate the membrane in the connector section and to penetrate the membrane in the head portion, thereby establishing a liquid channel via the liquid conduit between the interior of the liquid chamber and the interior of the fluid transfer component and a separate air channel via the air conduit between the interior of the air chamber and the interior of the fluid transfer component. The fluid transfer apparatus of the invention is characterized in that a hydrophobic filter is inserted in the air channel in at least one location between the air chamber and the fluid transfer component.

In embodiments of the apparatus of the invention a section of the air channel is located outside of the apparatus.

In embodiments of the apparatus of the invention the connector section comprises a hollow cylindrical outer body having:
- (a) a distal shoulder portion radially protruding from the outer body and terminating with an opening through which the proximal end of a fluid transfer component can be inserted for coupling;
- (b) a closed proximal cap having a central portion comprising connection means protruding proximally from it to connect to the syringe-like proximal portion of the apparatus;
- (c) a needle holder protruding into the interior of the outer body from a central portion of the closed proximal cap for retaining therein two conduits comprising sharp pointed ends and further provided with apertures through which liquid and air respectively are transferred during a fluid transfer operation; and
- (d) a double membrane seal actuator reciprocably displaceable within the hollow interior of the outer body The double membrane seal actuator comprises:
- (i) a cylindrical actuator casing;
- (ii) a proximal membrane that seals the proximal end of the casing
- (iii) a distal membrane that seals the distal end of the casing, wherein a part of the distal membrane protrudes distally from the casing; and
- (iv) at least one resilient arm which is connected at a proximal end thereof to an intermediate portion of the exterior of the casing and comprises an enlarged locking element at its distal end; the enlarged locking element having specifically shaped surface areas which interact with the inner wall of the hollow cylindrical outer body of the connector section to enable a four step procedure for connecting or separating the connector section to a fluid transfer component.

These embodiments can comprise a sleeve made of an elastic material that surrounds the tip and the distal opening of the needle of the air conduit inside the double membrane seal actuator.

In embodiments of the apparatus of the invention the connector section comprises a hollow cylindrical outer body having:
- (a) a distal shoulder portion radially protruding from the outer body and terminating with an opening through which the proximal end of a fluid transfer component can be inserted for coupling;
- (b) a closed proximal cap having a central portion comprising connection means protruding proximally from it to connect to the throat of the syringe-like proximal portion of the apparatus;
- (c) an elongated cylindrical needle holder protruding into the interior of the outer body from a central portion of the closed proximal cap for retaining therein two conduits comprising sharp pointed ends and further provided with apertures through which liquid and air respectively are transferred during a fluid transfer operation; and
- (d) a single membrane seal actuator reciprocably displaceable within the hollow interior of the outer body.

The single membrane seal actuator comprises:
- (i) a cylindrical actuator casing;
- (ii) a proximal O-ring that seals the proximal end of the casing to the outer surface of the elongated cylindrical needle holder;
- (iii) a distal membrane that seals the distal end of the casing, wherein a part of the distal membrane protrudes distally from the casing; and
- (iv) at least one resilient arm which is connected at a proximal end thereof to an intermediate portion of the exterior of the casing and comprises enlarged locking elements at its distal end; the enlarged locking element having specifically shaped surface areas which interact with the inner wall of the hollow cylindrical outer body of the connector section to enable a four step procedure for connecting or separating the connector section to a fluid transfer component.

These embodiments of the apparatus can comprise a sleeve made of an elastic material that surrounds the tip and the distal opening of the needle of the air conduit inside the single membrane seal actuator.

In embodiments of the apparatus of the invention the fluid transfer component is a vial adaptor that comprises an air channel and a separate liquid channel, thereby providing a closed transfer system that does not vent to or communicate with the environment.

In embodiments of the apparatus of the invention comprising a vial adaptor the vial adaptor comprises:
- (a) a distal collar portion comprised of a disk shaped central piece with a plurality of segments adapted for facilitating securement of the vial adaptor to a head portion of a medical vial or any type of vessel or device that has a head section similar to that of the head portion of a standard medicine vial, the segments attached to the circumference of the disk shaped central piece and projecting distally away from it;
- (b) a longitudinal extension projecting proximally from the disk shaped central piece the longitudinal extension adapted to be coupled to a fluid transfer device;
- (c) a membrane that seals the proximal end of the longitudinal extension;
- (d) a spike element which protrudes distally from the center of the disk shaped central piece;
- (e) an air channel and a liquid channel both of which are internally formed within the longitudinal extension and the spike element, the channels adapted to allow fluid communication through the vial adapter from the proximally located membrane to openings at the tip of the spike.

In these embodiments an annular shaped flat hydrophobic filter is located in the disk shaped central piece and the vial adaptor and the filter are adapted to allow fluid flowing in the liquid channel to pass through the vial adapter without passing through the filter and to force fluid flowing through the air channel to pass through the filter.

In embodiments of the apparatus of the invention comprising a vial adaptor the vial adaptor comprises:
- (a) a bottom part adapted to be attached to the head section of a medical vial or any type of vessel or device that has a head section similar to that of the head of a standard medicine vial;
- (b) a top part comprising:
  - (i) a disk shaped central piece and a plurality of wings adapted for facilitating securement of the top part to the bottom part, the wings attached to the circumference of the disk shaped central piece and projecting distally away from it;
  - (ii) a longitudinal extension projecting proximally from the disk shaped central piece, the longitudinal extension adapted to be coupled to a fluid transfer device;
  - (iii) a membrane that seals the proximal end of the longitudinal extension;
  - (iv) a spike element which protrudes distally from the center of the disk shaped central piece;

(v) an air channel and a liquid channel both of which are internally formed within the longitudinal extension and the spike element, the channels adapted to allow fluid communication through the vial adapter from the proximally located membrane to openings at the tip of the spike;

(c) a first locking mechanism; and (d) a second locking mechanism.

The first locking mechanism is adapted to lock the top part to the bottom part such that the tip of the spike cannot contact a stopper in the head section when the head section is being attached to the bottom part and to release the top part from the bottom part after the bottom part has been attached to the head section; and the second locking mechanism is adapted to allow, after the bottom part has been attached to the head section, the spike to penetrate the stopper in the head section and to irremovably lock the top part to the bottom part.

In these embodiments an annular shaped flat hydrophobic filter can be located in the disk shaped element and the vial adaptor and the filter adapted to allow fluid flowing in the liquid channel to pass through the vial adapter without passing through the filter and to force fluid flowing through the air channel to pass through the filter.

In embodiments of the apparatus comprising an annular shaped flat hydrophobic filter one or both of the outer and inner circumferential edges of the annular shaped flat hydrophobic filter are welded, glued, or mechanically pressed to the vial adaptor.

In embodiments of the apparatus comprising an annular shaped flat hydrophobic filter the annular shaped flat hydrophobic filter is supported by and lays on plurality of closely spaced supporting ribs from one or both of above and below.

Embodiments of the apparatus comprising an annular shaped flat hydrophobic filter comprise a by-pass comprising a one-way valve placed in parallel to the filter in the air channel. The one-way valve can be comprised of an elastic cap, which is tightly fit over an end of a rigid tube.

Embodiments of the apparatus comprising an annular shaped flat hydrophobic filter can comprise a selective valve in the air path located between the filter and the fluid transfer component to which or from which liquid is being transferred. The selective valve is activated by one of: electricity, pressure, or gravity.

In embodiments in which the selective valve is a gravity activated valve, the valve is comprised of a housing having a first opening on its side and a second opening on its end, a heavy weight inside of the housing, and an elastic layer connected to the end of the weight that faces the second opening. The dimensions of the weight and the elastic layer are such that the weight can move freely inside housing a short distance in a direction parallel to a longitudinal axis of housing such that: in a first vertical orientation, gravity pulls the weight downwards pressing the elastic layer onto the second opening, thereby preventing fluid from entering the housing through the second opening; and, an inverted vertical orientation, gravity pulls the weight and attached elastic layer away from the second housing, thereby allowing fluid to enter the housing through the second opening.

In a second aspect the invention is a vial adaptor comprising:

(a) a distal collar portion comprised of a disk shaped central piece and a plurality of segments adapted for facilitating securement of the vial adaptor to a head portion of a vial, the segments attached to the circumference of the disk shaped central piece and projecting distally away from it;

(b) a longitudinal extension projecting proximally from the disk shaped central piece;

(c) a membrane that seals the proximal end of the longitudinal extension;

(d) a spike element which protrudes distally from the center of the disk shaped central piece;

(e) an air channel and a liquid channel both of which are internally formed within the longitudinal extension and the spike element, the channels adapted to allow fluid communication through the vial adapter from the proximally located membrane to openings at the tip of the spike, thereby providing a closed transfer device that does not vent to or communicate with the environment.

An annular shaped flat hydrophobic filter is located in the disk shaped central piece and the vial adaptor and the filter adapted to allow fluid flowing in the liquid channel to pass through the vial adapter without passing through the filter and to force fluid flowing through the air channel to pass through the filter.

In a third aspect the invention is a vial adaptor comprising:

(a) a bottom part adapted to be attached to the head section of a medical vial or any type of vessel or device that has a head section similar to that of the head of a standard medicine vial;

(b) a top part comprising:

(i) a disk shaped central piece and a plurality of wings adapted for facilitating securement of the top part to the bottom part, the wings attached to the circumference of the disk shaped central piece and projecting distally away from it;

(ii) a longitudinal extension projecting proximally from the disk shaped central piece, the longitudinal extension adapted to be coupled to a fluid transfer device;

(iii) a membrane that seals the proximal end of the longitudinal extension;

(iv) a spike element which protrudes distally from the center of the disk shaped central piece;

(v) an air channel and a liquid channel both of which are internally formed within the longitudinal extension and the spike element, the channels adapted to allow fluid communication through the vial adapter from the proximally located membrane to openings at the tip of the spike, thereby providing a closed transfer device that does not vent to or communicate with the environment;

(c) a first locking mechanism; and (d) a second locking mechanism.

The first locking mechanism is adapted to lock the top part to the bottom part such that the tip of the spike cannot contact a stopper in the head section when the head section is being attached to the bottom part and to release the top part from the bottom part after the bottom part has been attached to the head section; and the second locking mechanism is adapted to allow, after the bottom part has been attached to the head section, the spike to penetrate the stopper in the head section and to irremovably lock the top part to the bottom part.

In embodiments of the vial adaptor of the third aspect of the invention an annular shaped flat hydrophobic filter is located in the disk shaped central piece, the vial adaptor and the filter adapted to allow fluid flowing in the liquid channel to pass through the vial adapter without passing through the filter and to force fluid flowing through the air channel to pass through the filter.

In embodiments of the vial adaptor of the vial adaptors of the first and second aspects of the invention one or both of the outer and inner circumferential edges of the annular shaped flat hydrophobic filter are welded, glued, or mechanically pressed to the vial adaptor.

In embodiments of the vial adaptor of the vial adaptors of the first and second aspects of the invention the annular shaped flat hydrophobic filter is supported by and lays on a plurality of closely spaced supporting ribs from one or both of above and below.

Embodiments of the vial adaptor of the vial adaptors of the first and second aspects of the invention comprise a by-pass comprising a one-way valve placed in parallel to the filter in the air channel. The one-way valve can be comprised of an elastic cap, which is tightly fit over an end of a rigid tube.

Embodiments of the vial adaptor of the vial adaptors of the first and second aspects of the invention comprise a selective valve in the air path located between the filter and the fluid transfer component to which or from which liquid is being transferred. The selective valve can activated by one of: electricity, pressure, or gravity.

Embodiments of a gravity activated valve comprise: a housing having a first opening on its side and a second opening on its end, a heavy weight inside of the housing, and an elastic layer connected to the end of the weight that faces the second opening. The dimensions of the weight and the elastic layer are such that the weight can move freely inside housing a short distance in a direction parallel to a longitudinal axis of housing allowing, in a first vertical orientation, gravity to pull the weight downwards pressing the elastic layer onto the second opening, thereby preventing fluid from entering the housing through the second opening; and, an inverted vertical orientation, gravity to pull the weight and attached elastic layer away from the second housing, thereby allowing fluid to enter the housing through the second opening.

All the above and other characteristics and advantages of the invention will be further understood through the following illustrative and non-limitative description of embodiments thereof, with reference to the appended drawings.

BRIEF DESCRIPTION OF THE DRAWINGS

FIG. 1 is a schematic cross-sectional view of a prior art apparatus for transferring hazardous drugs;

FIG. 2 schematically shows the concept of an aspect of the present invention;

FIG. 3a to FIG. 3d schematically show the 4 steps connection sequence between the connector section and the vial adaptor of the apparatus of FIG. 1;

FIG. 4a and FIG. 4b schematically show the concept of operating the apparatus for transferring hazardous drugs;

FIG. 5 shows the actual air channel of the prior art apparatus of FIG. 1; where both air channel ends serve as inlet and outlet respectively;

FIG. 6 symbolically shows possible places on the air channel of the drug transfer apparatus where a filter can be placed in accordance with the present invention;

FIG. 19 and FIG. 20 show an improvement in the double membrane seal actuator of FIG. 16 according to the present invention that simplifies manufacturing of the actuator;

FIG. 31 to FIG. 32b are detailed views showing a one way valve and its implementation when the air flows from the vial to the syringe and from the syringe into the vial respectively;

DETAILED DESCRIPTION OF EMBODIMENTS OF THE INVENTION

Figure 7:
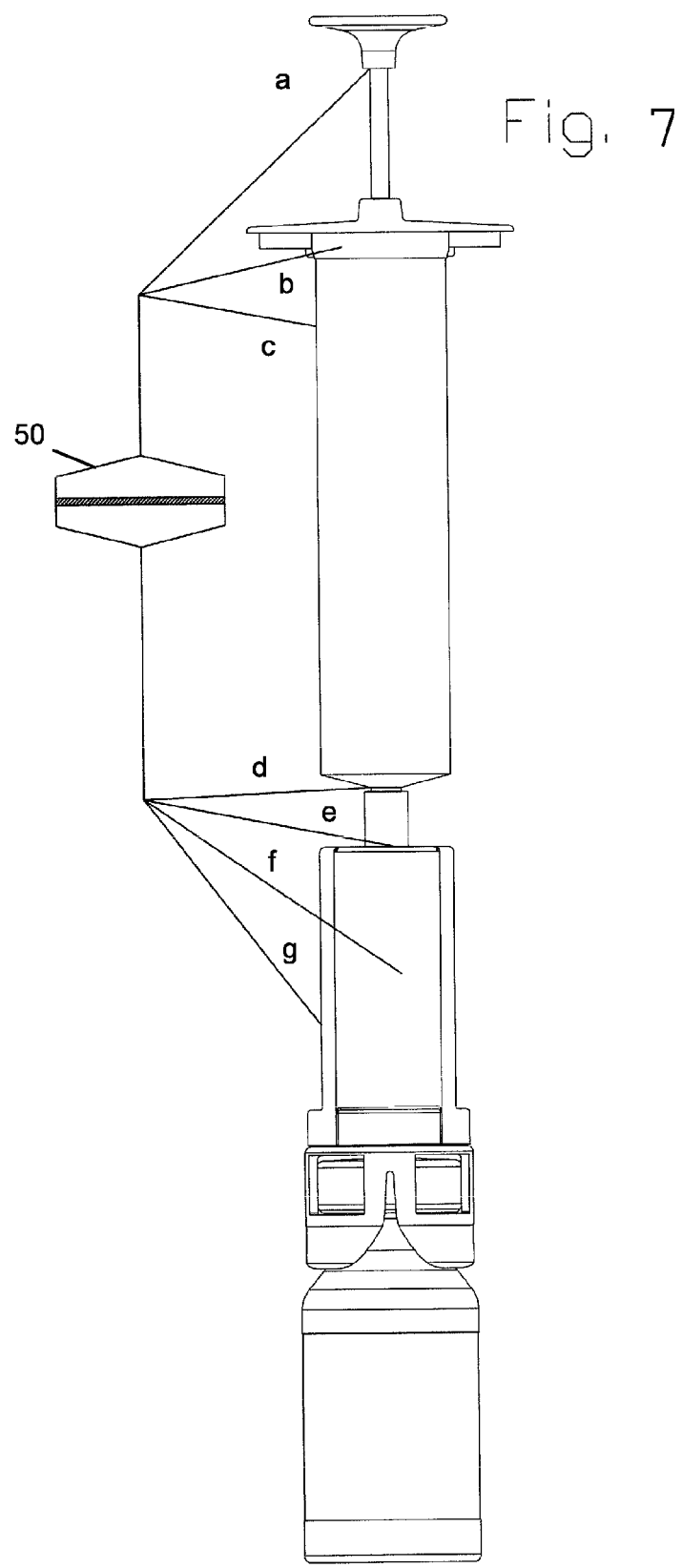
FIG. 7 symbolically shows an embodiment of liquid transfer apparatus in which the liquid channel is internal to the apparatus and air is exchanged between the vial and the proximal air chamber in the syringe via an air channel that is partially external to the apparatus.

The present invention is improvements to the drug transfer apparatus described in U.S. Pat. No. 8,196,614. These improvements overcome problems discovered during the commercial development of the apparatus and contribute to the safety of the transfer procedures carried out with them. Some of these improvements are specific to the embodiments of the apparatus described in U.S. Pat. No. 8,196,614 and others can be used with other prior art or new devices.

FIG. 2 schematically shows a first solution provided by the present invention to the problem of liquid being accidentally forced into the air chamber of the syringe. The solution, as shown symbolically in the figure is to introduce a hydrophobic filter membrane 50 at some point in the air channel 42 between the vial 16 and the proximal air chamber 32. Such a filter, e.g. a 0.22 micron filter, will not only prevent passage of liquid into the proximal air chamber but also will improve the protection against microbial contamination by additional filtering the air.

FIG. 5 schematically shows the air transfer path inside the apparatus 10 from one end, symbolically shown by arrow 52, at the tip of the spike in the vial to its other end, symbolically shown by arrow 54, at the opening in the distal end of the hollow piston rod.

FIG. 6 symbolically shows some of the possible locations in the air channel of the drug transfer apparatus where a filter can be placed in accordance with the present invention. The locations shown in FIG. 6 are: (a) at the proximal end of the long air conduit 38; (b) in the piston rod 24 installed on the proximal end of the air conduit 38; (c) at the opening in the distal end of the hollow piston rod 24; (d) between syringe 12 and connector section 14 at the throat 20 of the syringe; (e) in the double membrane seal actuator 34; (f) at the proximal end of the air conduit 38 and the distal end of the elastic membrane 15a of vial adaptor 15; (g) in the vial adaptor just above the spike; and (h) in the air channel inside the spike.

This aspect of the present invention can be used with embodiments of liquid transfer apparatuses other than that described herein above. For example, FIG. 7 symbolically shows an embodiment of liquid transfer apparatus in which the liquid channel is internal to the apparatus (identical to that described herein above) and air is exchanged between the vial and the proximal air chamber in the syringe via an air channel that is partially external to the apparatus. In this embodiment the proximal end of the external portion of the air channel can be connected to the proximal air channel in the syringe for example: (a) through the hollow piston rod; (b) through the gasket 22 at the top of the syringe; or (c) directly through the wall of the proximal end of body 18 of the syringe. The distal end of the external portion of the air channel can be connected to the air channel from the vial 16 through the vial adaptor 15 and connector section 14 for example: (d) at the connection between the throat 20 of the syringe and connector section 14; (e) at the top of air conduit 38 (in this embodiment air conduit 38 is short and does not extend into the interior of the piston rod as in the embodiment of FIG. 1); (f) in the double membrane seal actuator 34; or (g) through the side wall of the cylindrical hollow outer body of the connector section 14.

FIGS. 8 to 15 show the currently used embodiment of the invention in which a filter is introduced into the air channel by placing it in the vial adaptor 15. This is the location that has been determined to be the most effective and technically simple one to manufacture. Vial adaptors of this design can be used not only with the liquid transfer apparatus described in U.S. Pat. No. 8,196,614 that is manufactured by the applicant of the present application but also with device for transferring liquid from a vial or (suitably modified) from some other type of fluid transfer component.

Figure 8:
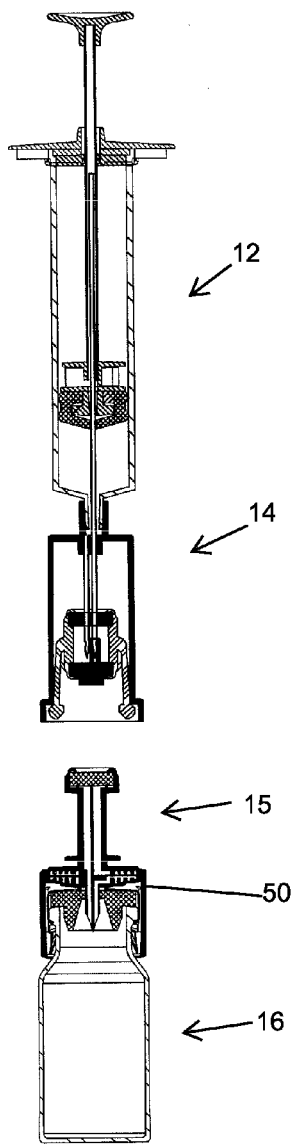
FIG. 8 to FIG. 15 show an embodiment of the invention in which a filter is introduced into the air channel by placing it in the vial adaptor.

FIG. 8 shows the syringe 12 with attached connector section 14 a moment before they are connected to the vial adaptor 15, which has been modified by integrating a filter 50 according to the present invention.

Figure 9:
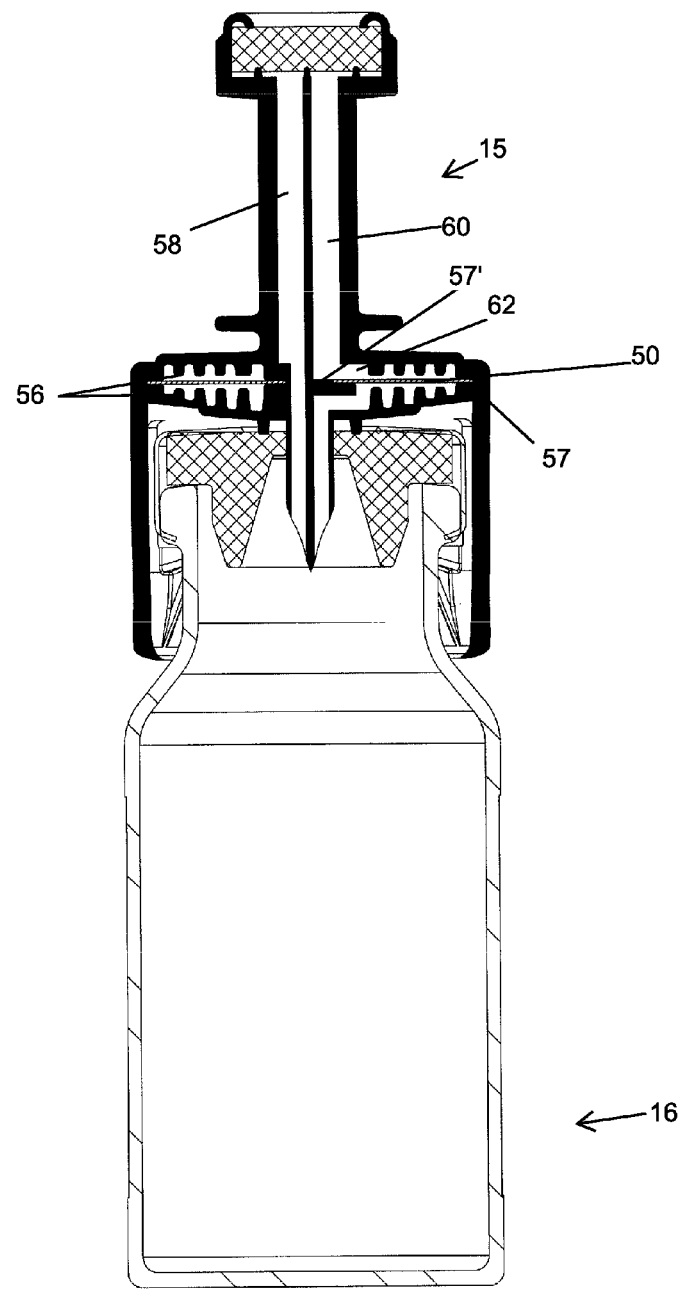

FIG. 9 is an enlarged cross-sectional view of the modified vial adaptor 15 attached to vial 16. In the figure can be seen the liquid channel 58 and the air channel 60 through the vial adaptor 15 and filter 50. The filter is made of a very thin disc shaped piece of material. A hole is cut through it to allow free passage of liquid through liquid channel 58. The filter 50 is welded or glued or mechanically pressed to the vial adaptor at its outer circumference 57 and inner circumference 57'.

Pressure exerted on filter 50 by air or liquid flowing through air channel 60 could be great enough to tear the filter or to cause it to become crumpled or to clog the filter 50 by the liquid—even to the extent that channel 60 becomes blocked. Therefore to provide mechanical support to withstand pressures, to prevent tearing, and to keep the filter straight and flat filter 50 is placed between a plurality of closely spaced supporting ribs 56 from above and below.

Figure 10:
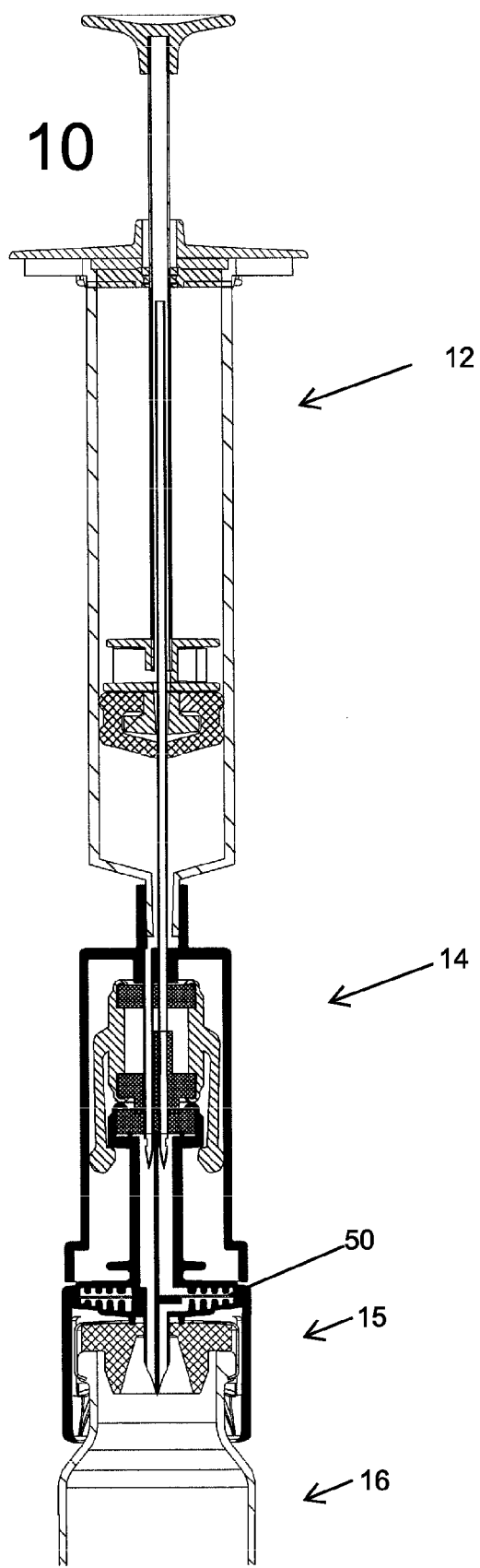

FIG. 10 shows the assembled fluid transfer apparatus comprising syringe 12, connector section 14, vial adaptor 15 with filter 50, and vial 16.

Figure 11:
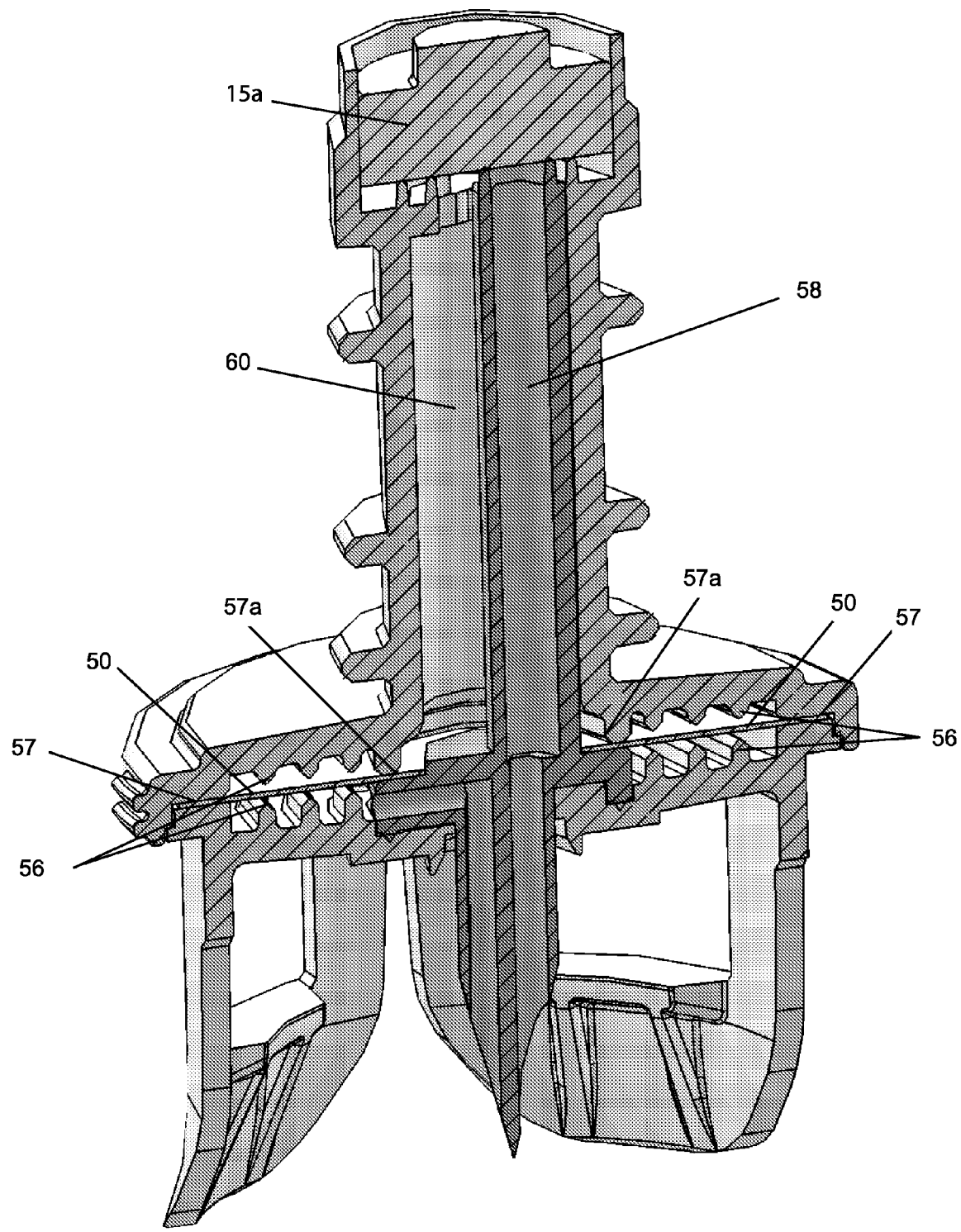
Figure 12:
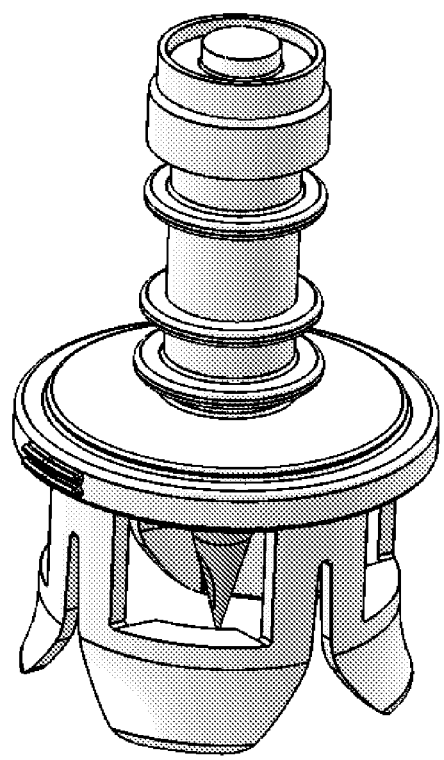

FIG. 11 is a cross-sectional view and FIG. 12 is a prospective view of a vial adaptor comprising a filter that has been developed by the applicant of this patent application. The vial adaptor is manufactured as five separate parts that are shown in the following figures and then assembled as shown in FIG. 11. The five parts are: membrane 15*a*, filter 50, the spike assembly, the upper and the lower sections of the vial adaptor.

Figure 13A:
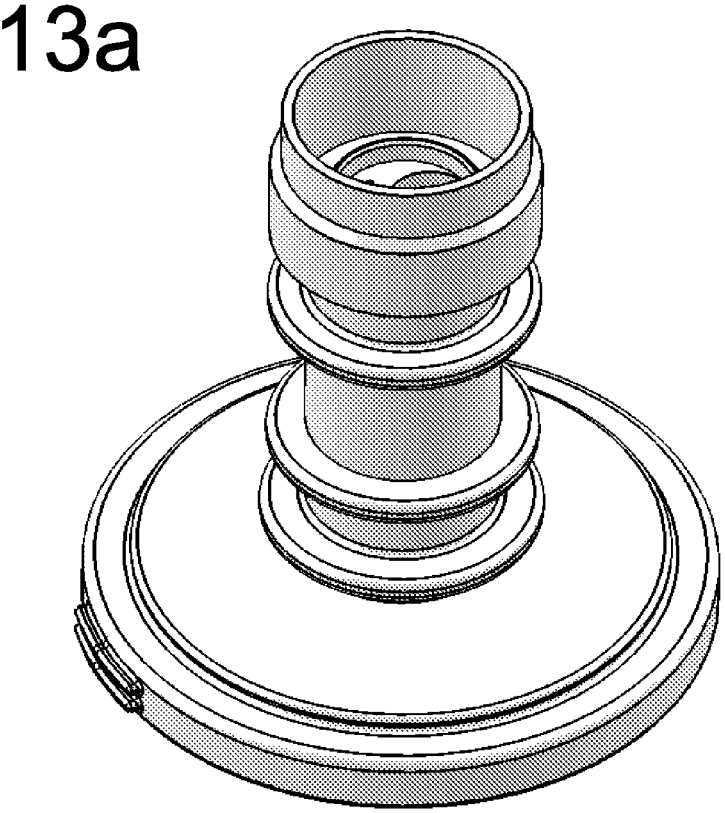
Figure 13B:
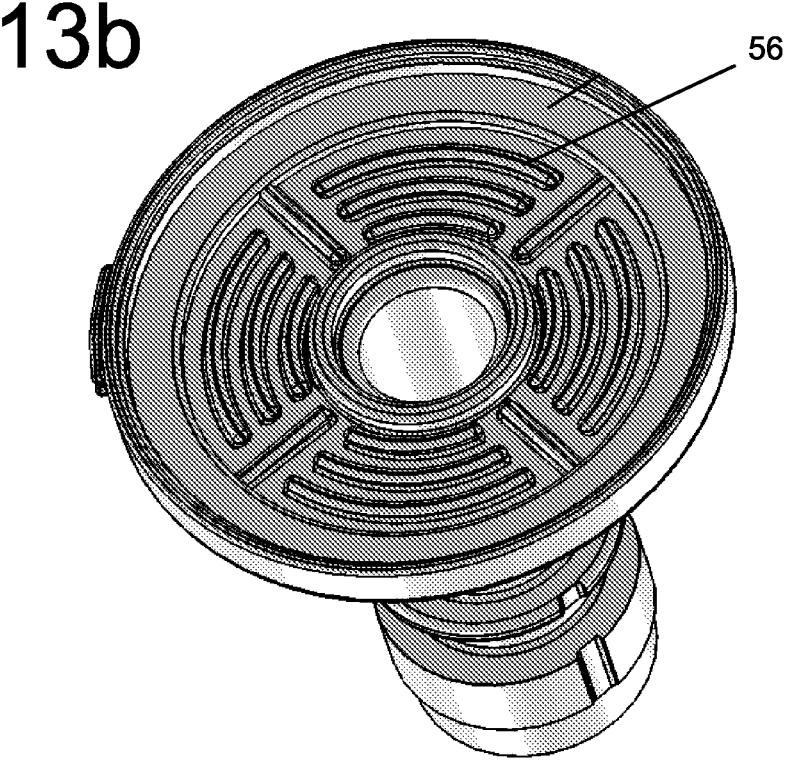

FIG. 13*a* and FIG. 13*b* respectively show top and bottom views of the upper section of the vial adaptor. This section comprises a tubular structure through which the air channel 60 and upper part of the spike assembly (see FIG. 11 and FIG. 15) passes and the membrane seats on its upper surface and a plurality of ribs 56 on its flat round lower surface to support the filter against damage/breakage when forces are applied on the filter.

Figure 14A:
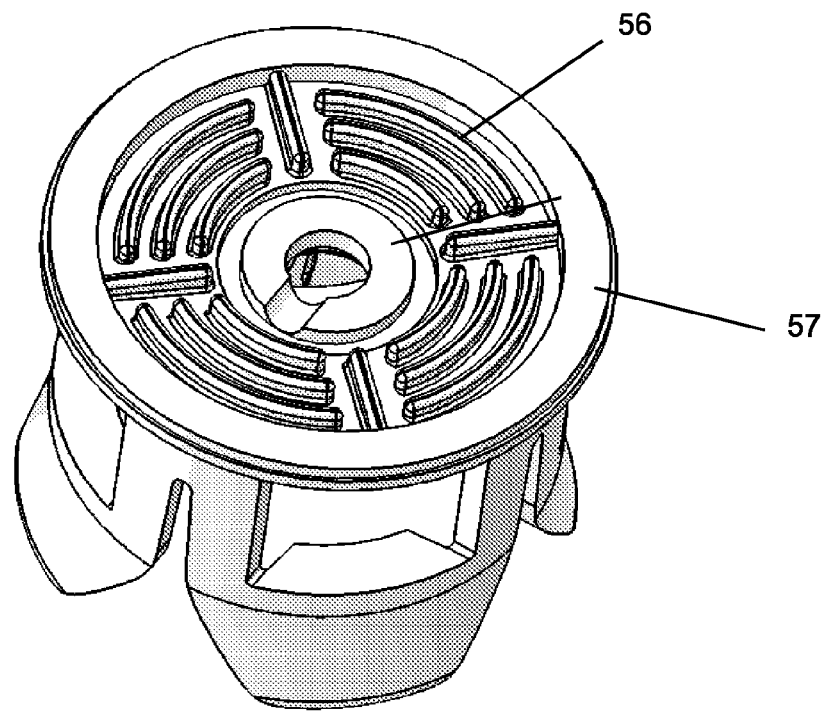
Figure 14B:
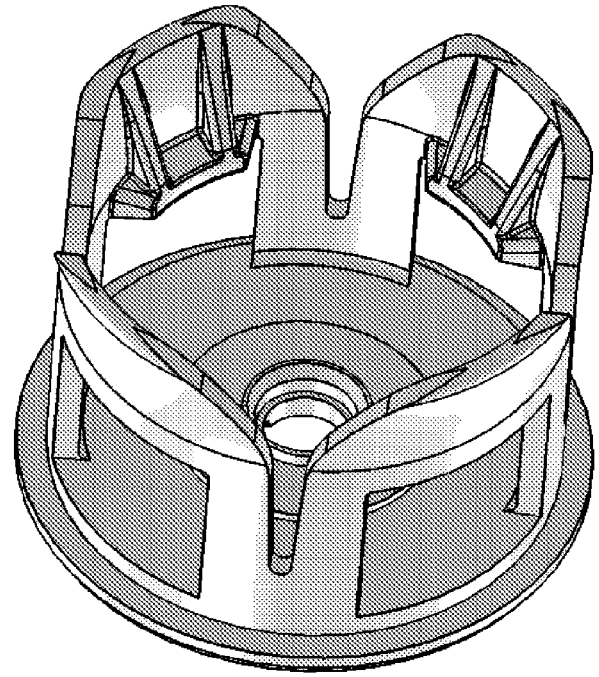

FIG. 14*a* and FIG. 14*b* respectively show top and bottom views of the lower section of the vial adaptor. This section comprises a plurality of circumferential segments formed with ledges on the inner face thereof, for securement to the head portion of a vial on its lower end a plurality of ribs 56 on its flat round upper surface to support the filter against damage/breakage when forces are applied on the filter. The platform 57*a* is made for welding the outer circumference 57 of the filter 50 to it.

Figure 15:
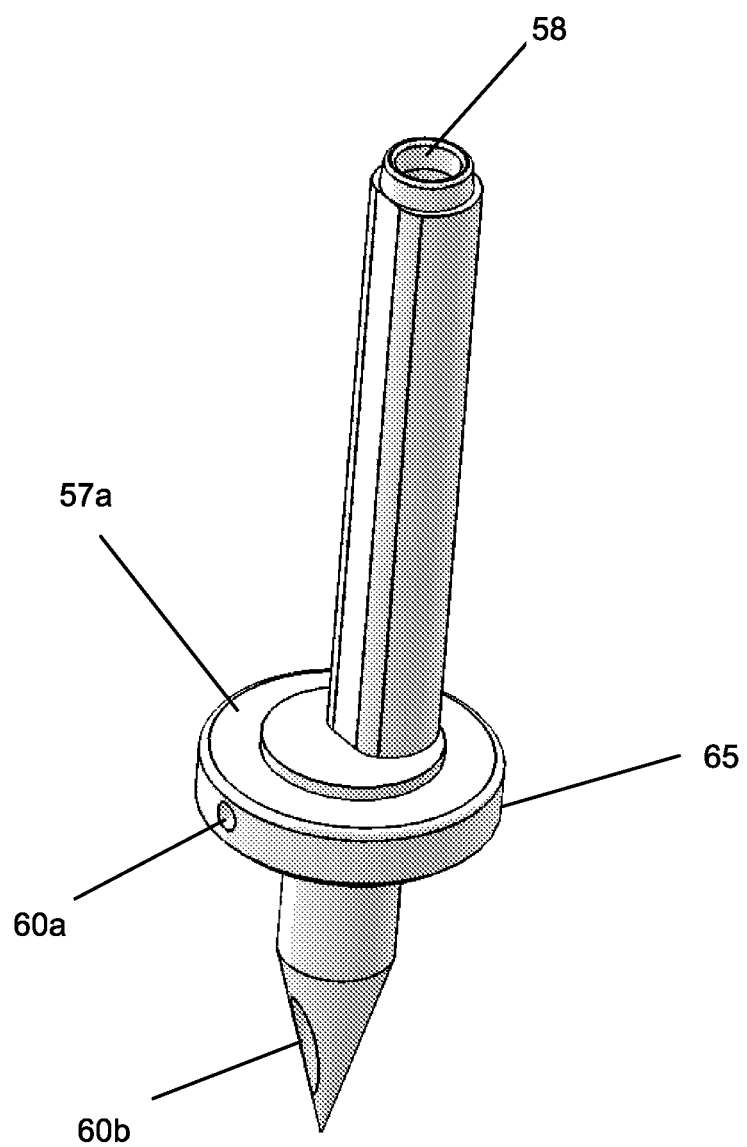

FIG. 15 shows the spike assembly of the vial adaptor, which comprises the spike on its lower end and a tubular structure through which the liquid channel 58 passes. The small opening 60*a* on the side of the disk shaped platform 65 above the spike is one end of the air channel 60 just below the distal side of the filter 50, which sits on top of platform 65. From this opening the air channel goes through the spike and terminates at the opening 60*b* on the spike tip. The flat top side of the disc 65 serves as a platform for welding the inner circumference 57' of filter 50 to it. Besides welding other methods known in the art for attaching the filter, such as sealing by heat, ultrasonic or laser welding, gluing, mechanically sealing and pressing, and more are applicable to this invention. The bottom side of the disc 65 serves as a welding or gluing platform for attaching the spike assembly to the lower section of the vial adaptor that is shown in FIG. 14*a*

Figure 16:
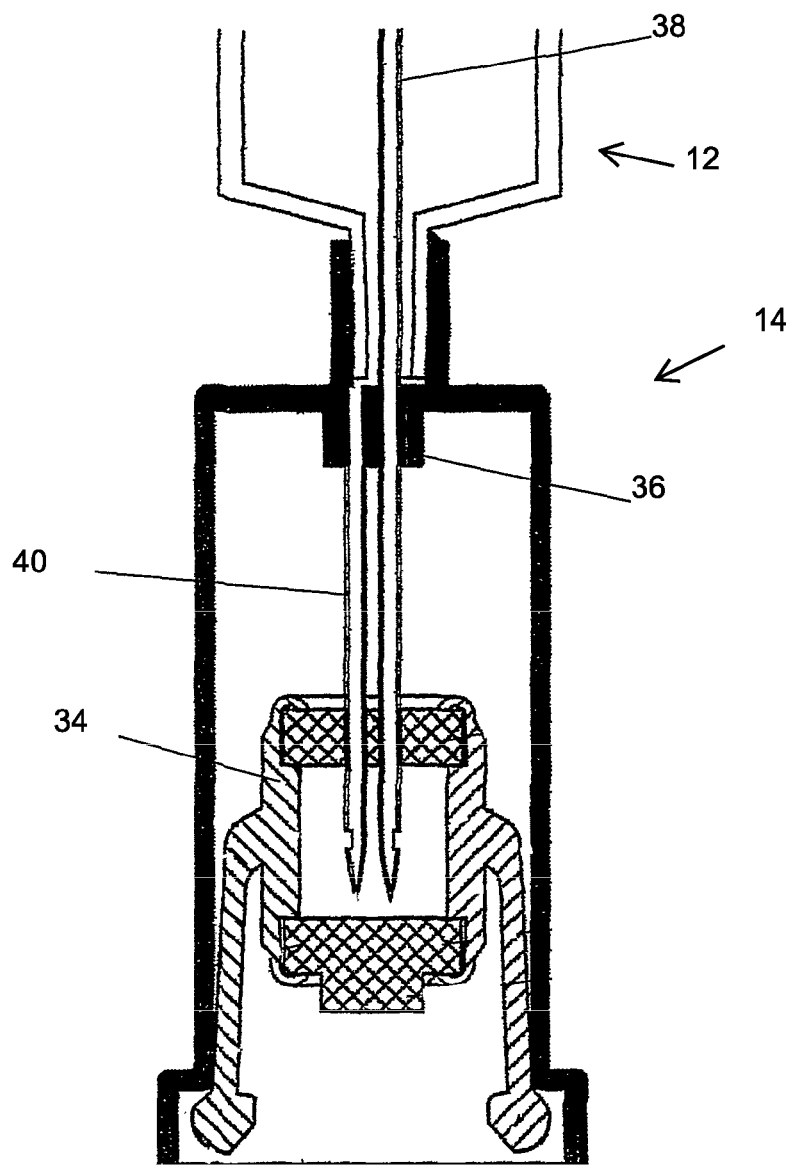
FIG. 16 is an enlarged view of the prior art double membrane seal actuator shown in FIG. 1.
Figures 17, 18:
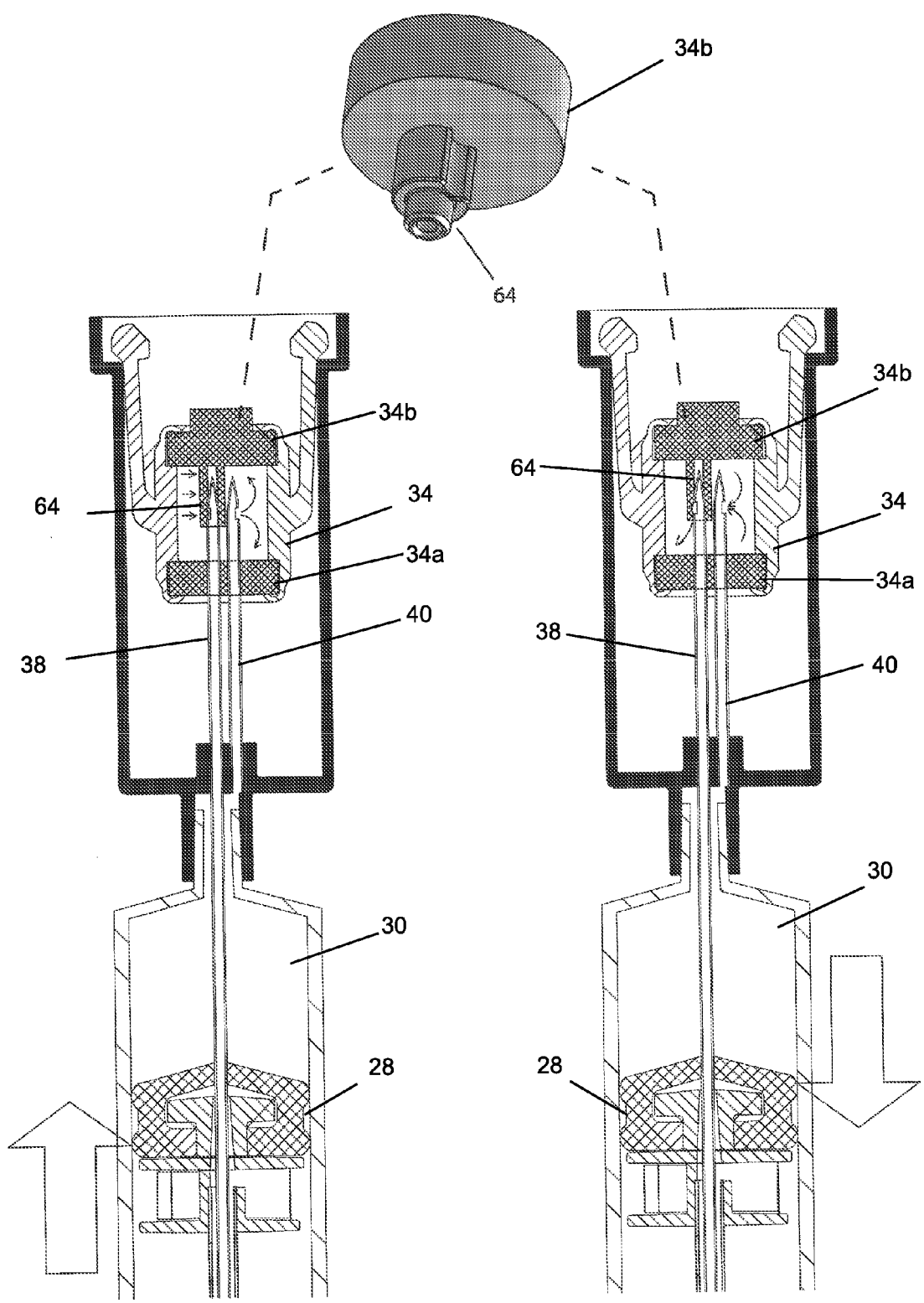
FIG. 17 and FIG. 18 show an improvement in the double membrane seal actuator of FIG. 16 according to the present invention that prevents the possibility of liquid entering the air channel if the piston rod of the syringe is accidently pushed or pulled.

FIGS. 16 to 18 show another aspect of the present invention, i.e. an improvement in the double membrane seal actuator 34 of the connector section 14 that prevents the possibility of liquid entering the air channel if the piston rod of the syringe is accidentally pushed or pulled when the syringe connector is not connected to a vial adaptor or other component of a drug transfer apparatus.

FIG. 16 is an enlarged view of the prior art connector section 14 of the drug transfer apparatus shown in FIG. 1. As described herein above, when syringe 12 and attached connector section 16 are not connected to another component, the tips of the needles that are the air conduit 38 and liquid conduit 40 reside between the proximal and distal membranes of double membrane seal actuator 34. If the piston rod of the syringe is pushed in a distal direction, then liquid that is in the liquid chamber below the piston of the syringe will be forced out of the opening at the distal end of needle 40 and can be pushed into the opening at the distal end of needle 38 and forced into the air chamber above the piston syringe. If the piston rod is pulled distally, then the opposite flow of air and liquid takes place and air can be forced from the air chamber into the liquid chamber of the syringe.

The solution provided by the present invention is a sleeve 64 into which the tip of the needle 38 of the air conduit is placed. Sleeve 64 is made of an elastomeric material and is placed inside the double membrane seal actuator 34.

As shown in FIG. 17, when liquid chamber 30 contains liquid and the piston 28 of the syringe is pushed distally the fluid that is forced out of the tip of the liquid needle 40 creates pressure inside actuator 34 that causes sleeve 64 to be pressed around the tip of the air needle 38, thus blocking the passage of liquid into the air needle. The harder one pushes on the piston rod—the more effective is the blocking action of the sleeve. Additionally at same time, suction is created in the air chamber of the syringe on the proximal side of piston 28 and in the air needle 38 causing the sleeve 64 to be pressed even more tightly against the tip of the air needle, thereby increasing the blocking action.

As shown in FIG. 18, when the piston 28 of the syringe is pulled proximally the liquid needle 40 is in suction mode, creating vacuum in the interior of actuator 34. At same time the air needle 38 injects air into the interior of actuator 34 thus air pushing sleeve 64 away from the tip of needle 38 and expanding its diameter thereby allowing air to flow out of the air needle 38 into the liquid needle 40. From FIGS. 17 and 18 it can be seen that a one-way valve operation is taking place, i.e. liquid can't pass to the air channel or air chamber in the syringe, but air can pass to liquid chamber. The ability to draw air into the liquid chamber is purposely desired since it is required for certain manipulations during drug preparation.

FIG. 19 and FIG. 20 show another improvement in the prior art double membrane seal actuator shown in FIG. 16. This aspect of the present invention simplifies manufacturing of the double membrane actuator. According to this embodiment, the length of needle holder 36 that fixedly supports the needles that form air channel 38 and liquid channel 40 is lengthened and its shape is made cylindrical with a circular cross section. Additionally the proximal membrane 34a is removed and is replaced with an O-ring 66 that fits tightly over the exterior of needle holder 36.

FIG. 19 shows the connector section 14 when it is not connected to the vial adaptor 15. In this configuration the O-ring 66 is at the distal end of the needle holder 36 and the tips of the air and liquid conduits are above the lower membrane 34b of the actuator. As the connector section and vial adaptor are pushed together, the actuator is pushed in the proximal section with the O-ring 66 sliding up the needle holder 36 until it reaches the proximal end of the connector section and the needles have penetrated the lower membrane 34b of the actuator and the membrane at the top of the vial adaptor as shown in FIG. 20.

FIG. 21a to FIG. 28 show a novel type of vial adaptor designed to overcome the problem of tearing of the rubber stopper in the vial resulting from inaccurate insertion of the spike of the vial adaptor. The vial adaptor of the invention is comprised of two parts—a bottom part adapted to be attached to the head of a medical vial or any type of vessel or device that has a head section similar to that of the head of a standard medicine vial; and a top part that is adapted to be coupled to the bottom part and also to a medical transfer device such as the connector section of the drug transfer apparatus described herein above or a syringe.

The method of operation of this vial adaptor is to keep the spike enclosed and at distance from the rubber stopper of the vial until the vial adaptor is properly placed and locked on the head portion of the vial. At this locked stage the spike has not yet contacted the stopper. The proper positioning and locking achieved in this way insures that the spike is fixed in a centered and perpendicular position in relation to the rubber stopper. Only then is the vial adaptor ready to be further advanced with an axial motion to guide the spike to precisely pierce the stopper until, in its final position, the vial adaptor is irremovably locked to the vial.

It is important to emphasize that the procedure is described herein as comprising several steps; however, this is for ease in describing the procedure only. It is to be realized that in actual practice the secured engagement procedure using the present invention is carried out using a single smooth axial movement.

Figure 21B:
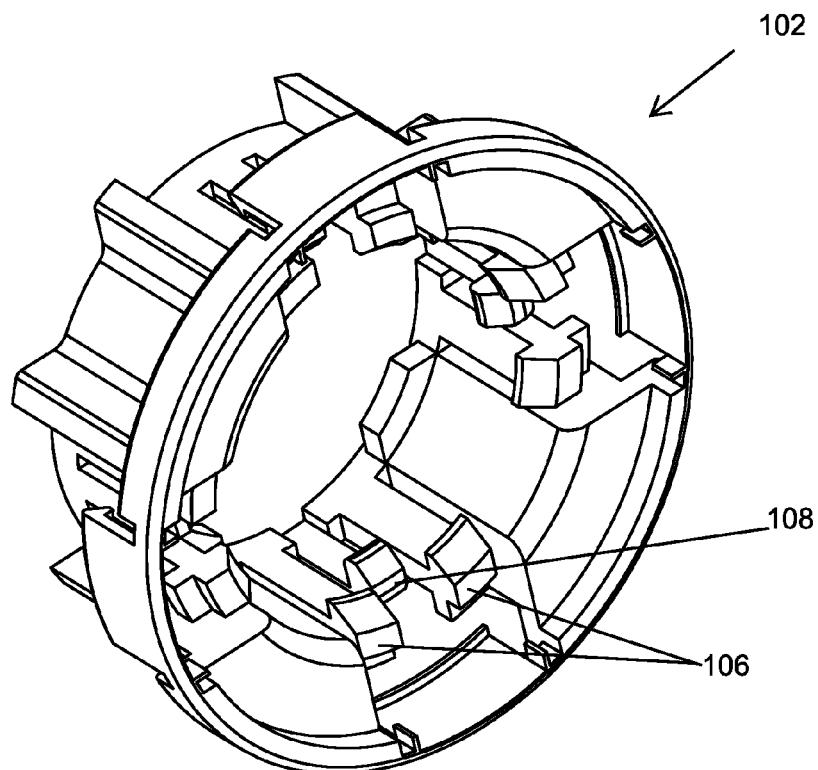
FIG. 21a to FIG. 28 show a vial adaptor designed to overcome the problem of tearing of the rubber stopper in the vial resulting from inaccurate insertion of the spike.
Figure 21A:
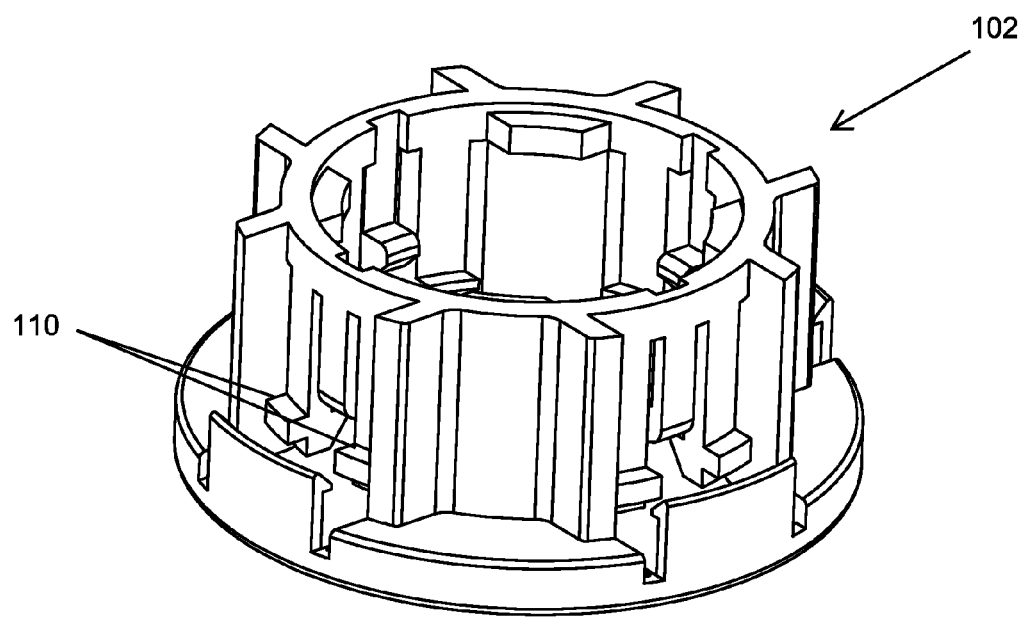

FIGS. 21a and 21b are perspective drawings showing different views of the bottom part 102 of the vial adaptor of the invention. Bottom part 102 is a generally cylindrical structure with a hollow interior. The lower part of the structure has an inside diameter slightly larger than that of the cap of the vial to which it will be connected. On the inside of the lower part of bottom part 102 are a plurality of inwardly facing teeth 106. Teeth 106 are on the end of flexible arms that allow teeth 106 to be pushed radially outward and then to snap back into their original position when the force on them is removed. Also seen on the inside of the lower part of bottom part 102 are a plurality of inwardly facing teeth 108 associated with teeth 106. On the outside of the arms to which teeth 106 are attached there are projections 110 for locking together the two parts of the vial adaptor.

Figure 22:
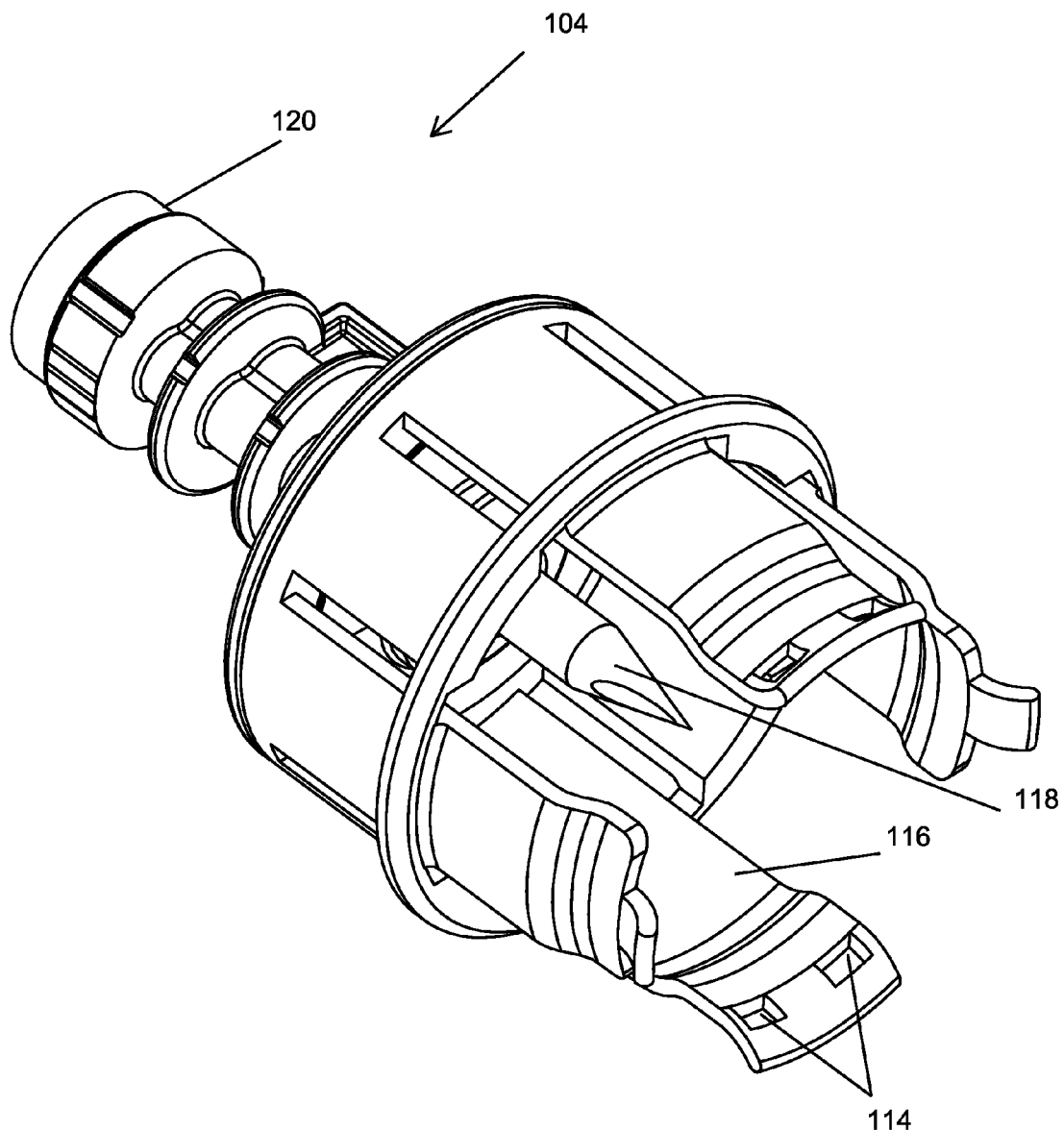
Figure 23:
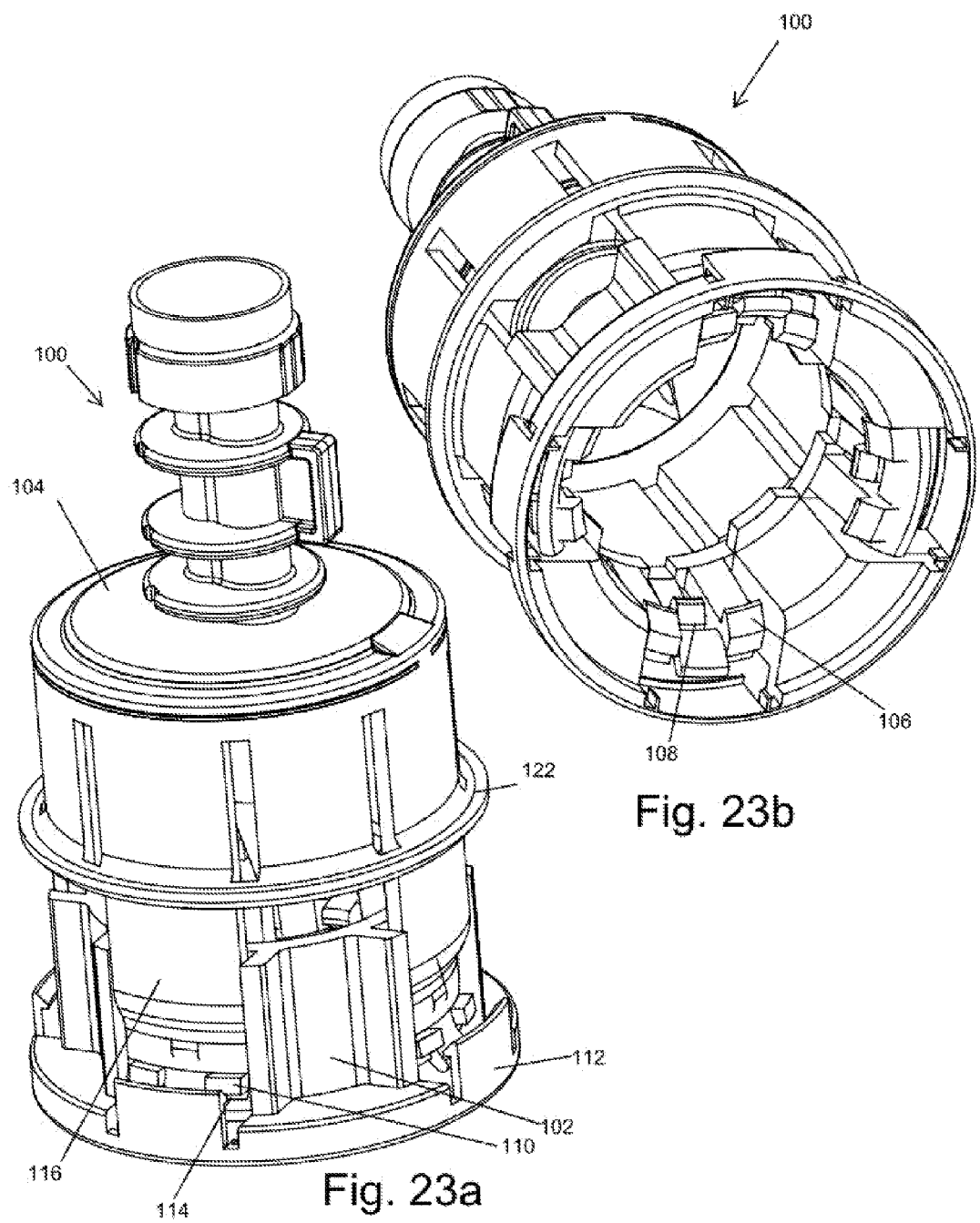

FIG. 22 shows the top part 104 of the vial adaptor. Top part 104 is a generally cylindrical structure. In the center of the structure is a downward projecting spike 118 that is in fluid communication with an upwardly projecting structure 120 designed to connect in a standard way to another component of a drug transfer system. Projecting downward are at least two wings 116, some of which have windows 114 in them that play a role in connecting the upper part 104 to the lower part as will be explained herein below.

FIGS. 23a and 23b are perspective drawings showing different views of the vial adaptor 100. Top part 104 has been slipped over and locked to bottom part 102 in a first locked configuration. In FIG. 23a it can be seen how the projections 110 on the bottom part 102 fit into windows 114 on the wings 116 of top part 104 to accomplish the locking together of the two parts of vial adaptor 100, so they can't move in respect to each other even when pushed. Also seen in FIG. 23a are snaps 112 with inwardly facing teeth on the bottom edge of bottom part 102 and an outwardly facing ledge 122 around the circumference of top part 104. Snaps 112 and ledge 122 interact to lock top part 104 to bottom part 102 in a second locked configuration to be described herein below.

FIG. 24 to FIG. 27 show different stages in the attachment of vial adaptor 100 to a vial.

Figure 24:
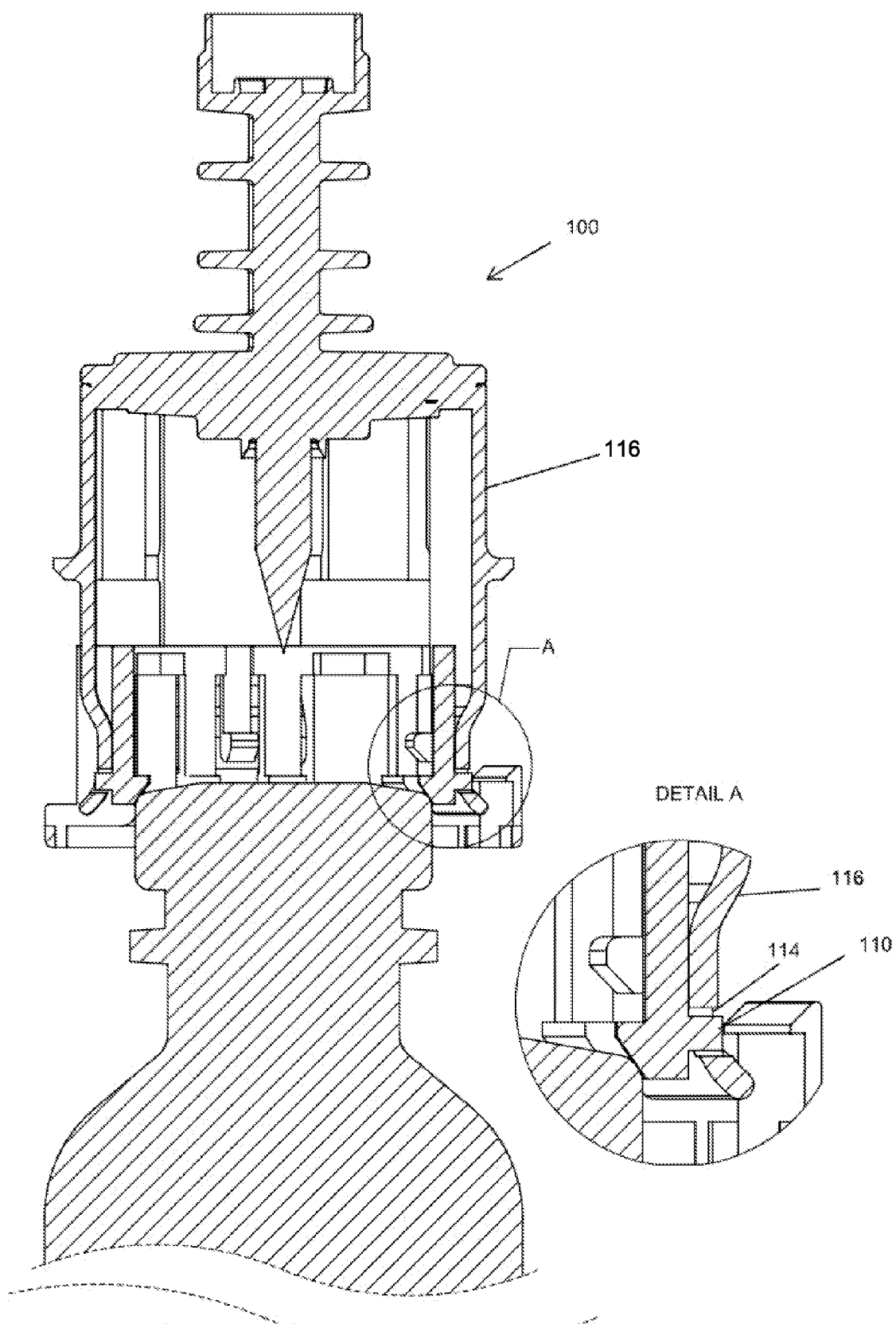

In the first stage, shown in FIG. 24, the cap of the vial has not yet entered the interior of the bottom part of vial adaptor 100. In the enlarged detail A it is seen how the projections 110 of bottom part 102 fit into windows 114 on wings 116 of upper part 104 locking the two parts together.

Figure 25:
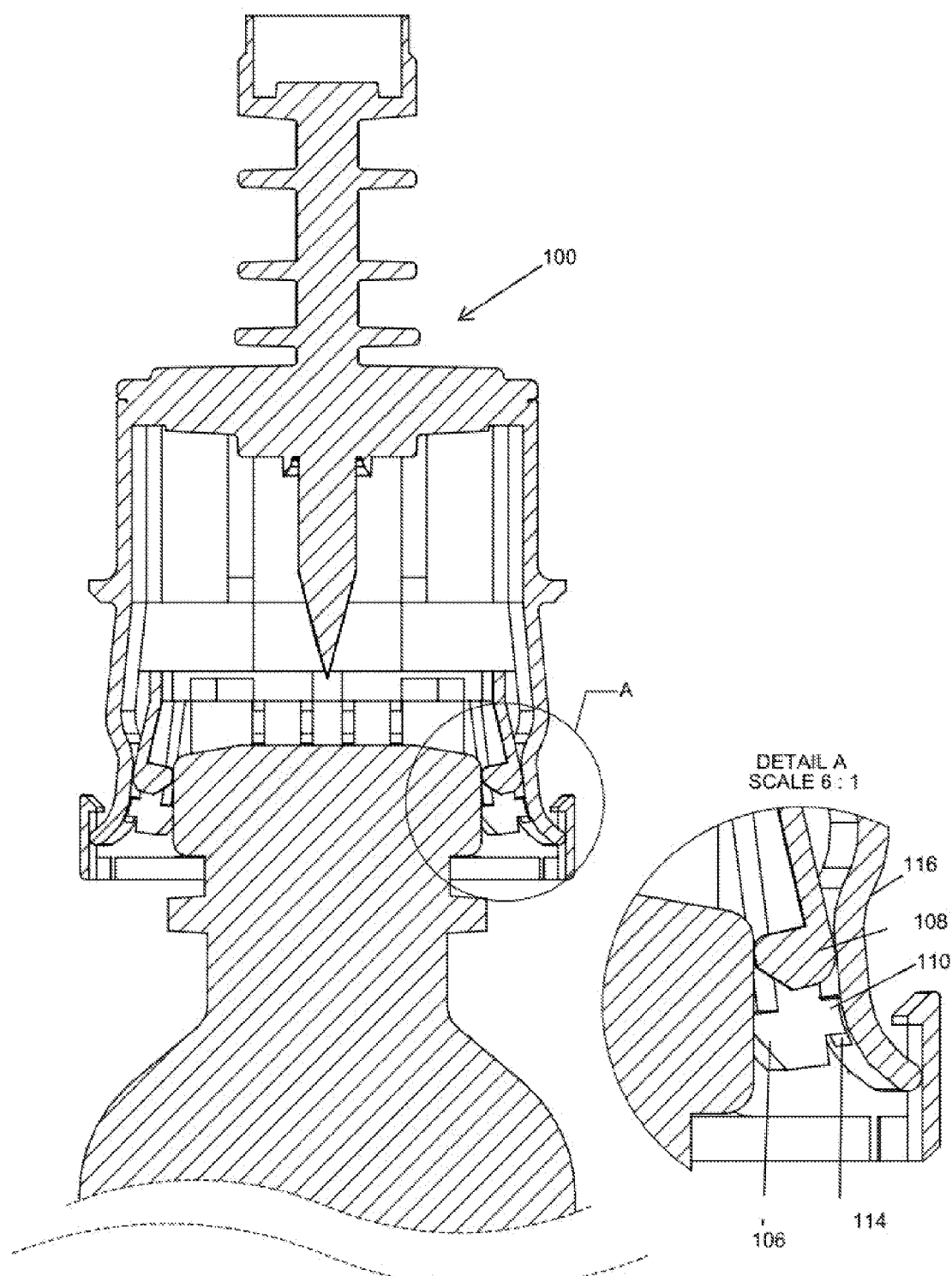

In the second stage, shown in FIG. 25, the cap of the vial is beginning to enter the interior of the bottom part of vial adaptor 100. In the enlarged detail A it is seen how the how the teeth 106 and the teeth 108 are pushed radially outward by the cap of the vial while the wings 116 are pushed radially by the back side of the teeth 108. Projections 110 of bottom part 102 are pushed into the windows 114 on wings 116 of upper part 104 keeping the two parts locked together and not yet allowing the parts 104 and 102 to slide into each other.

Figure 26:
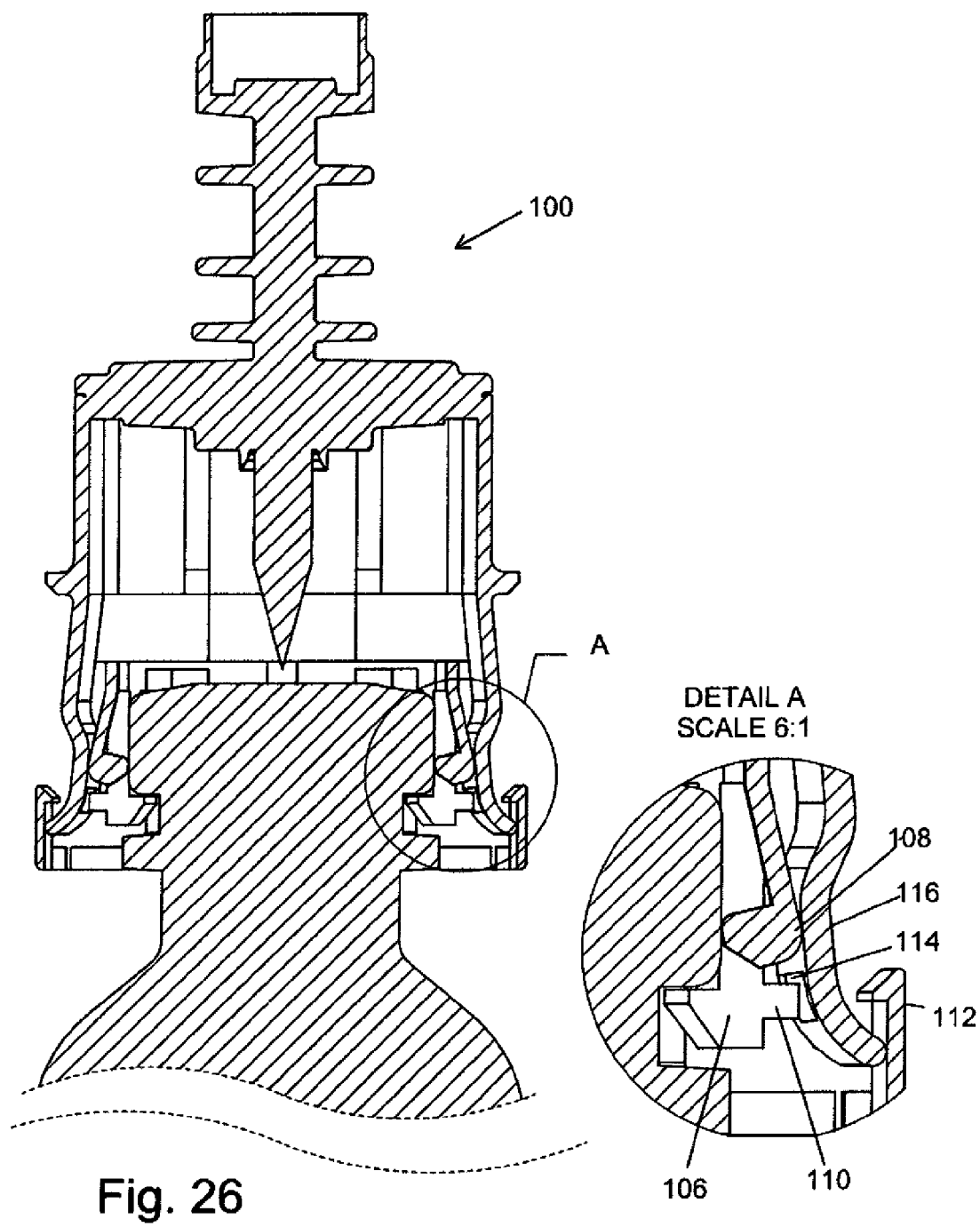
Figure 27:
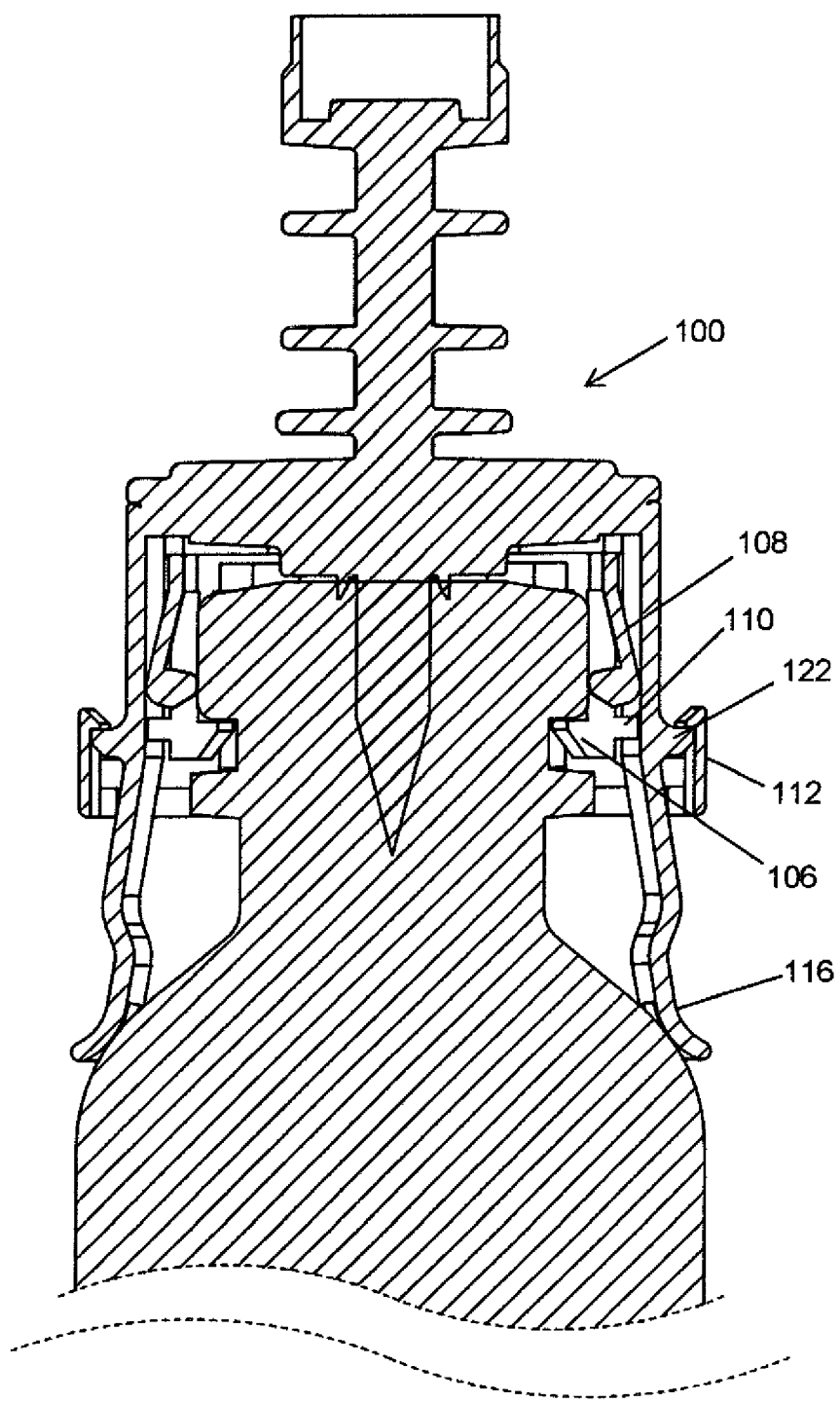

In the third stage, shown in FIG. 26, the cap of the vial has entered the interior of the bottom part of vial adaptor 100 to the end. In the enlarged detail A it is seen how the teeth 108 continue to push wing 116 radially outward. At the same time, the cap of the vial is no longer pushing the teeth 106 outwards allowing the arm to which teeth 106 and projections 110 are attached to spring radially inwards. As a result, teeth 106 move under the edge of the cap firmly attaching vial to the vial adaptor 100 and projections 110 of bottom part 102 are pulled out of the windows 114 on wings 116 of upper part 104 thereby breaking the lock between the two parts.

It should be noticed that at this stage the spike has not yet contacted the stopper in the top of the vial; for this to happen all locks must open, which indicates that the adaptor is fully attached and that the spike is in a centered and perpendicular position in relation to the vial rubber stopper and is ready to pierce precisely. If even one of the locks is not open the parts 102 and 104 will not move until all are in position and unlocked. As a consequence when in the fourth stage, shown in FIG. 27, the top part 104 of vial adaptor is pushed downward towards the vial, the spike is pushed through the vial stopper exactly in the center and perpendicular to the vial stopper. As the top part 104 slides over the bottom part 102, wings 116 slide over and grip the sides of the vial adding more stability to the connection. Eventually the teeth on the top of snaps 112 slide over the top of ledge 122 locking both parts of vial adaptor 100 together, thus prohibiting reverse motion that could pull the spike out of the vial. In embodiments of the vial adaptor snaps 112 are constructed so that both an audible sound as well as visual observation will confirm to the user that the attachment process has been completed.

Figure 28:
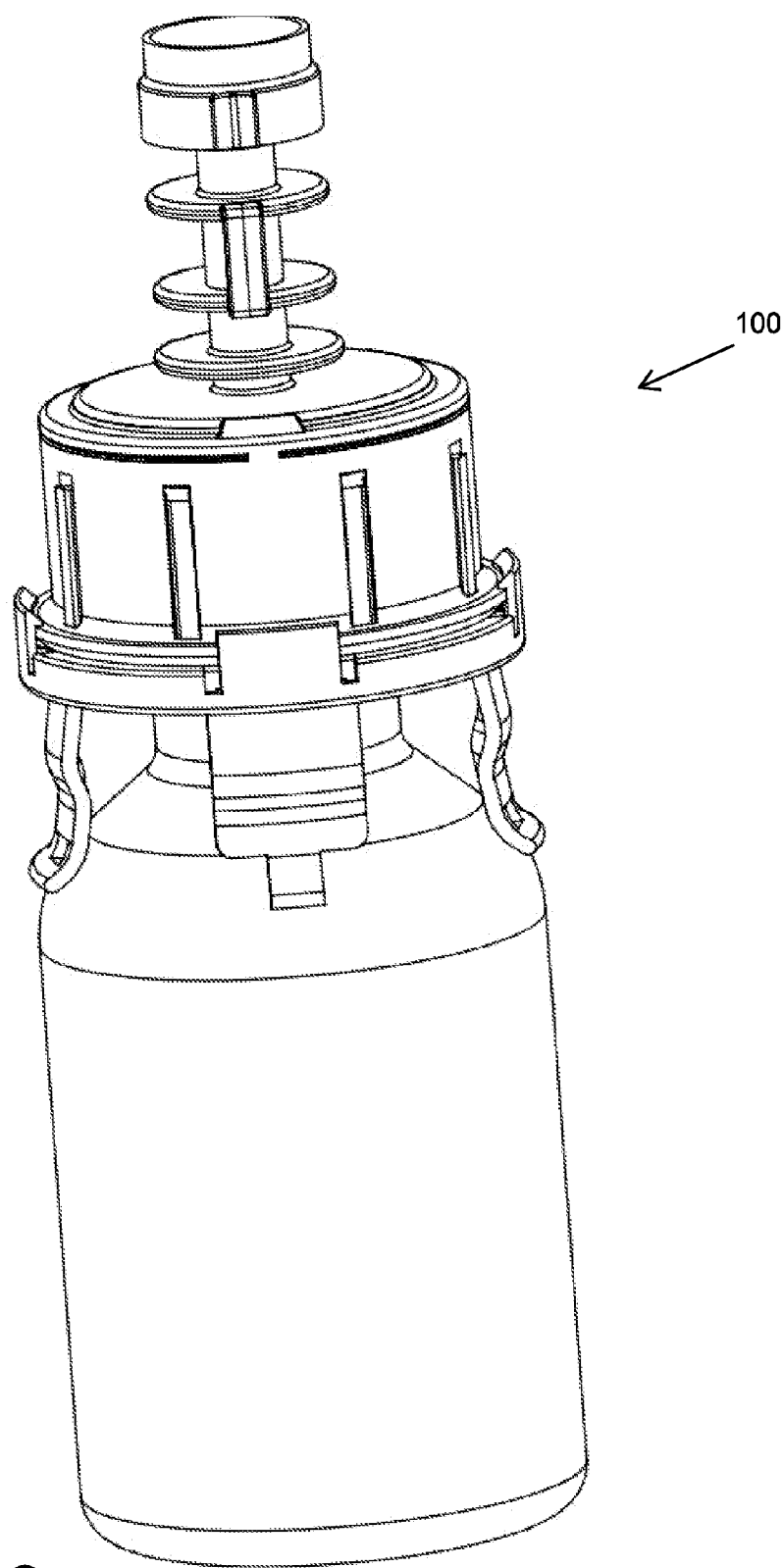

FIG. 28 shows vial adaptor 100 of the invention irremovably attached in its final position to a medical vial. An embodiment of vial adaptor 100 designed to be coupled to transfer devices such as those described herein above can be provided with a filter located, for example, in the top part 104 above the spike as described above.

When, as described herein above, hydrophobic filters are provided to serve as a barrier against water intrusion into the air channel of the fluid transfer apparatus, the filters may clog when liquid is pressed with pressure into the pores of the filter. Further, since hydrophobicity depends on the surface tension properties of the liquid, some liquids, such as alcohol, could easier cause clogging of the filter. Longer exposure time to liquid is another factor that influences and reduces the hydrophobicity performance.

In normal use conditions of the fluids transfer apparatus only slight clogging of the filter may occur, which can be easily unclogged by reversing the pressures. But in some cases of misuse or error by the operator the filter might remain permanently clogged, thus disabling the essential pressure equalization system.

The present invention seeks to provide a complete solution for the problem of clogging of the filter. The solution of the invention includes one or both of: 1) protecting the filter from high pressures, thus preventing permanent clogging of the filter; and 2) providing a bypass in case the filter is permanently clogged.

Bypass Solution

The following improvement is made to overcome the clogged filter by a one-way bypass, which in case of clogged filter, will bypass it and will allow unhindered withdrawal of drug from the vial and the flow of air from the air chamber of the syringe into the vial for the purpose of pressure equalization. The bypass is actually a one way valve placed in parallel to the filter on the air channel.

Figure 29:
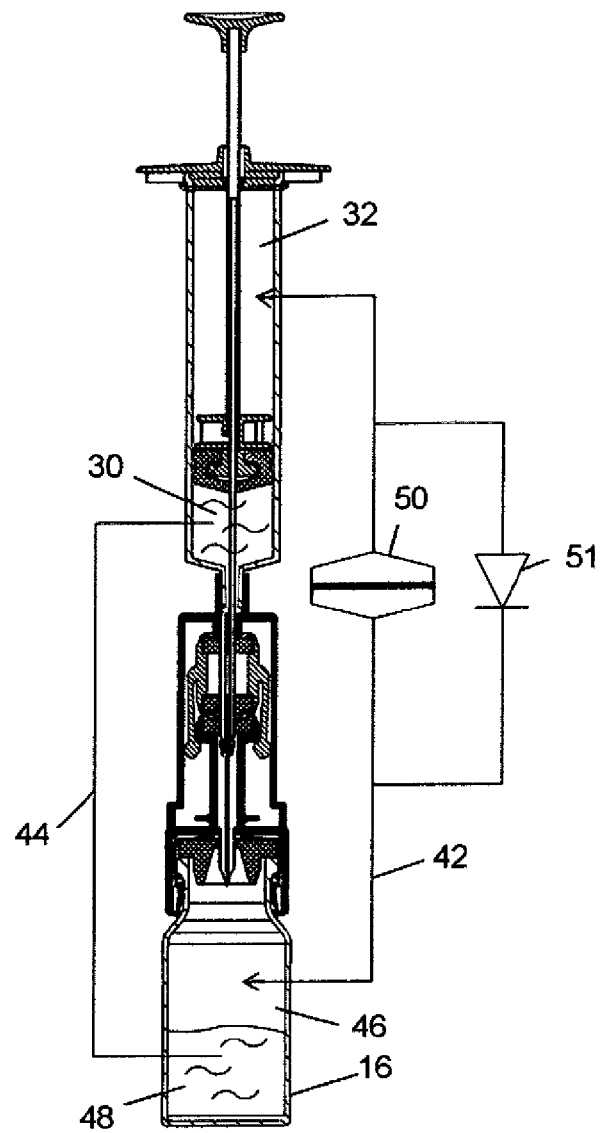
FIG. 29 schematically shows the flow diagram of an embodiment of the drug transfer apparatus comprising a one-way-valve in parallel to a filter on the air channel.

FIG. 29 schematically shows the flow diagram of the drug transfer apparatus, which is basically same as in FIG. 2, but with the addition of the one-way-valve 51 in parallel to the filter 50 on the air channel 42. During a withdrawal procedure the air can flow for pressure equalization, from the air chamber 32 in the back of the syringe to the vial 16. During that flow the air can pass through the filter 50 or the one way valve 51 or through both. In case of reversed flow, such as during an injection procedure, the air can flow from the vial 16 through the filter 50 to the air chamber, but it can't flow through the one way valve 51. In case that liquid flows from the vial instead the air, then the filter stops the liquid and the one way valve also blocks any flow through.

Figure 30:
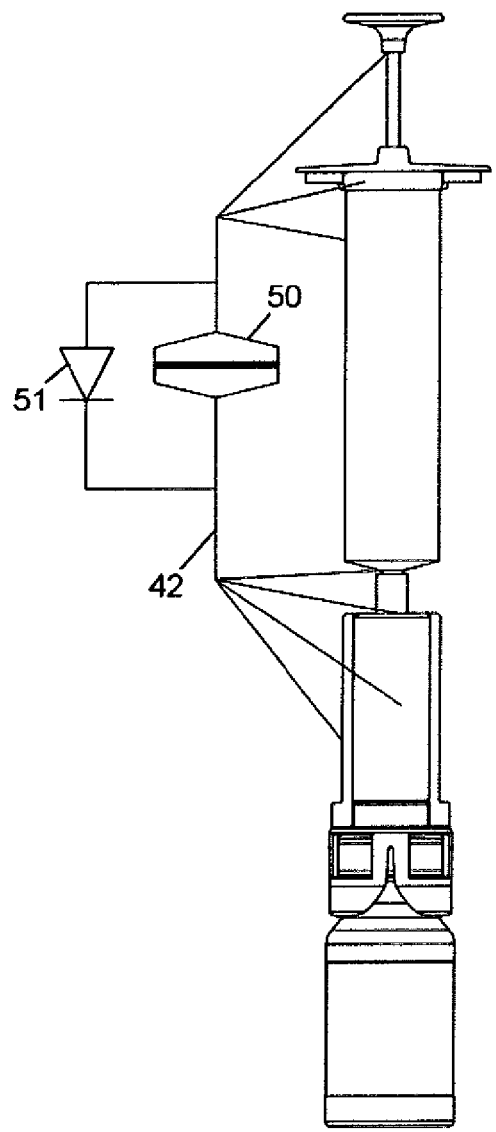
FIG. 30 schematically shows the embodiments shown in and described in relation to FIG. 7, but with the addition of a one-way-valve parallel to the filter in the air channel.

FIG. 30 schematically shows the embodiments shown in and described in relation to FIG. 7, but with the addition of a one-way-valve parallel to the filter in the air channel. FIG. 30 like FIG. 7 shows embodiments of the apparatus in which the air channel runs external to the syringe as well as a variety of connecting areas for the two ends of the air channel.

Figure 31:
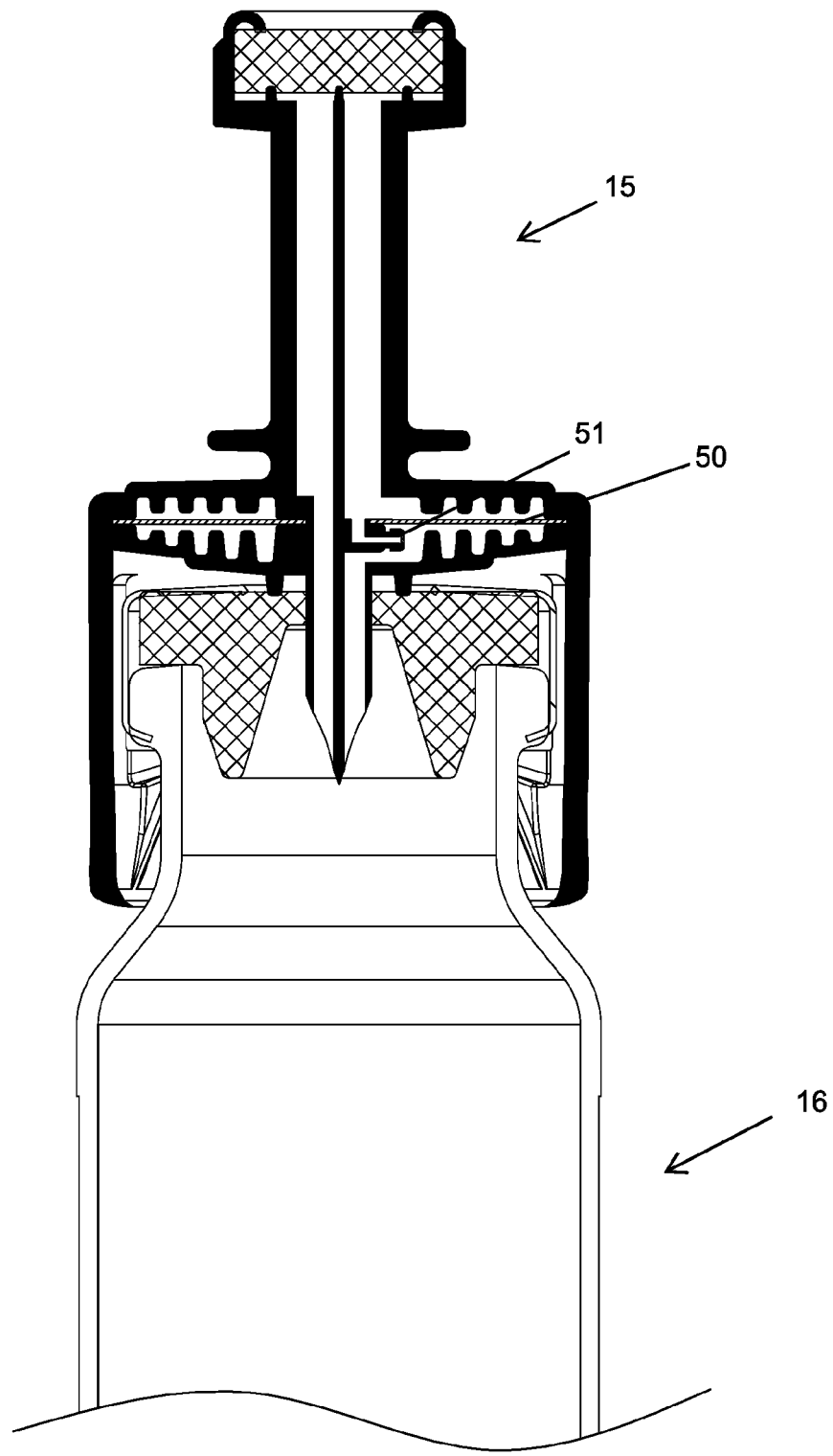

FIG. 31 schematically shows the embodiment of a vial adaptor 15 shown in and described in relation to FIG. 9, but with the addition of a one-way-valve 51 placed in parallel to the filter 50 in the air channel.

FIG. 32*a* and FIG. 32*b* are detailed views of the one way valve 51 and its implementation when the fluids flow from the vial to the syringe and from the syringe into the vial respectively. The one-way valve 51 is an elastic cap 55, which is tightly fit over the end of a rigid tube 53, which is a bypass to the filter 50 in the air conduit through which the flow of air between syringe and vial takes place. One-way valve 51 is a normally closed valve.

When air or liquid flow from the vial towards the filter, as shown in FIG. 32*a*, they can only flow through the filter 50 and are blocked from flowing through tube 53 by the cap 55. The higher the pressure that is applied on the valve cap, the tighter the cap is pushed against the outer wall of the tube. Thus air can flow into the syringe through the filter while liquid is stopped by both the filter and by the one way valve.

When air flows from syringe to the vial, such as during a procedure of withdrawing liquid from the vial as shown in FIG. 32*b*, the air can flow through the filter 50 and/or through the one way valve 51. If the filter 50 is clogged, the air will naturally enter the tube 53 and will create pressure from inside out on the cap 55 and will force it to expand and allow the air to flow between the outside of the tube 53 and the internal walls of the cap 55.

When the operator stops the withdrawal process the pressure inside the cap 55 drops and the cap 55 re-seals on its tube/seat.

FIG. 33 to FIG. 41 show an embodiment of a vial adaptor with filter and a bypass one-way valve implemented. In these figures can be seen a step by step, component by component, assembly of the vial adaptor for convenient understanding of its structure. Most of the features of the vial adaptor have been previously described in relation to the embodiments shown in FIG. 11 to FIG. 15 and FIG. 21*a* to FIG. 28 and thus only the most relevant parts relating to understanding the features of this embodiment will be identified in the figures.

Figure 33:
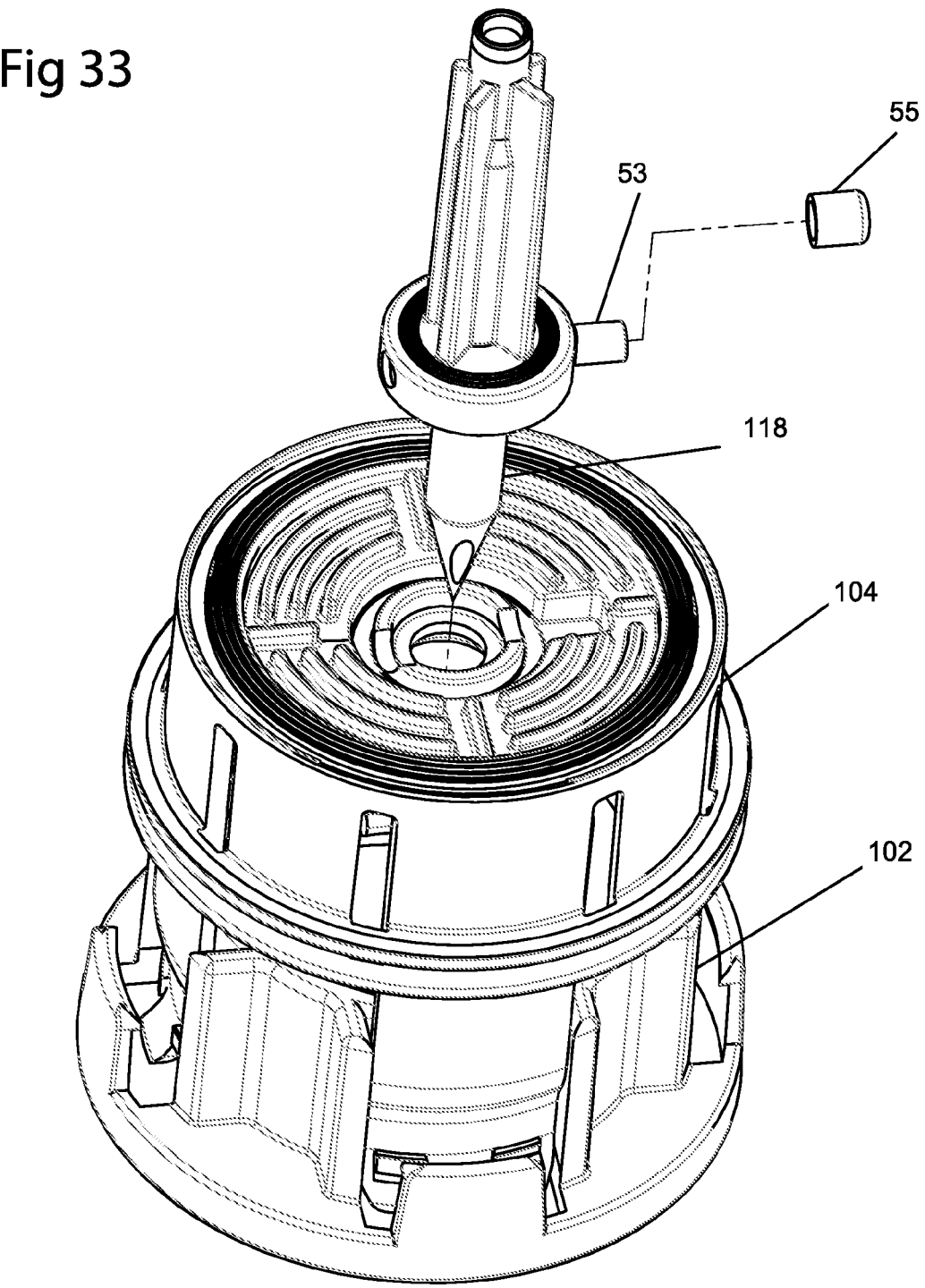
FIG. 33 to FIG. 41 show an embodiment of a vial adaptor with filter and a bypass one-way valve implemented.

In FIG. 33 can be seen the spike 118 component (see similar FIG. 15) before it is welded in place. The elastic cap 55 which will be put over the sideward extending tube 53 from the spike component, thus creating a one way valve is seen in the figure. In this embodiment the vial adaptor is the same novel type of vial adaptor attachment mechanism as described in FIGS. 21*a* to 28, designed to overcome the problem of tearing of the rubber stopper in the vial resulting from inaccurate insertion of the spike of the vial adaptor. For clarity and simplicity, the bottom part 102 of the vial adaptor will not be shown in the following figures. The component at the top of the drawing to which the spike component will be welded is the top part 104 of the vial adaptor shown in FIG. 22.

Figure 34:
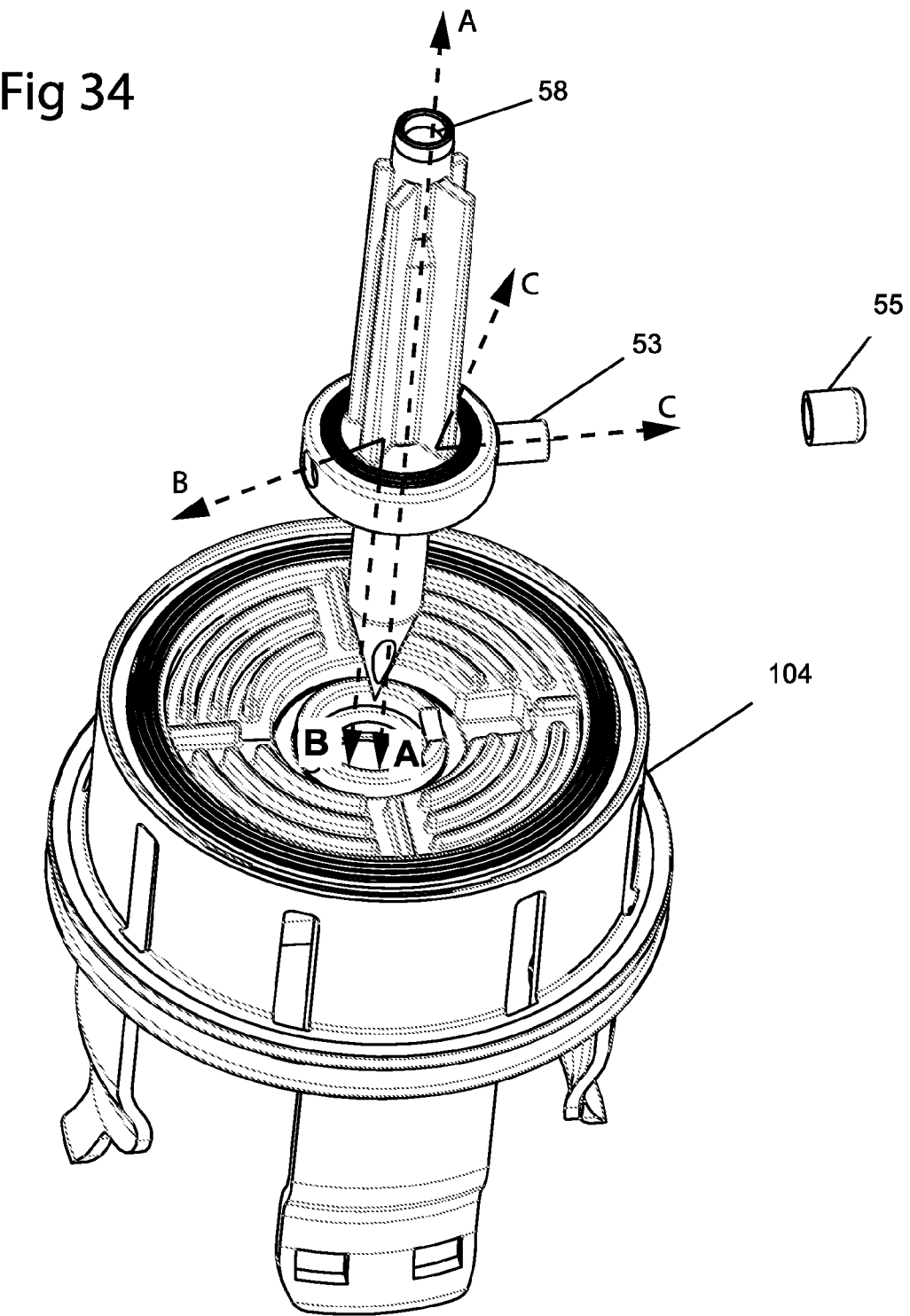

FIG. 34 shows the flow channels through the spike component. The flow channel marked A-A is the liquid channel 58 that goes in a straight line from the spike tip at the bottom, up to the top of the tube into which the liquid needle 40 of the syringe enters when the syringe is engaged with the adaptor.

The flow channel marked B-B is one end of the air channel. It starts at one of two openings 60b on the spike tip (see FIG. 15—not visible in this figure) and exits at a side opening 60a on the spike component. Once the spike component is welded to the top part 104 of the adaptor the opening 60b will be just below the filter (as will be seen in the following figures).

The flow channel C-C is the one way valve. The elastic cap 55 will be pushed onto the sideward extending tube 53 of channel C-C, thus creating a one way valve. The other end of the channel C-C is not covered by the filter and has access to the part of the air channel that goes directly to the air chamber of the syringe.

Figure 35:
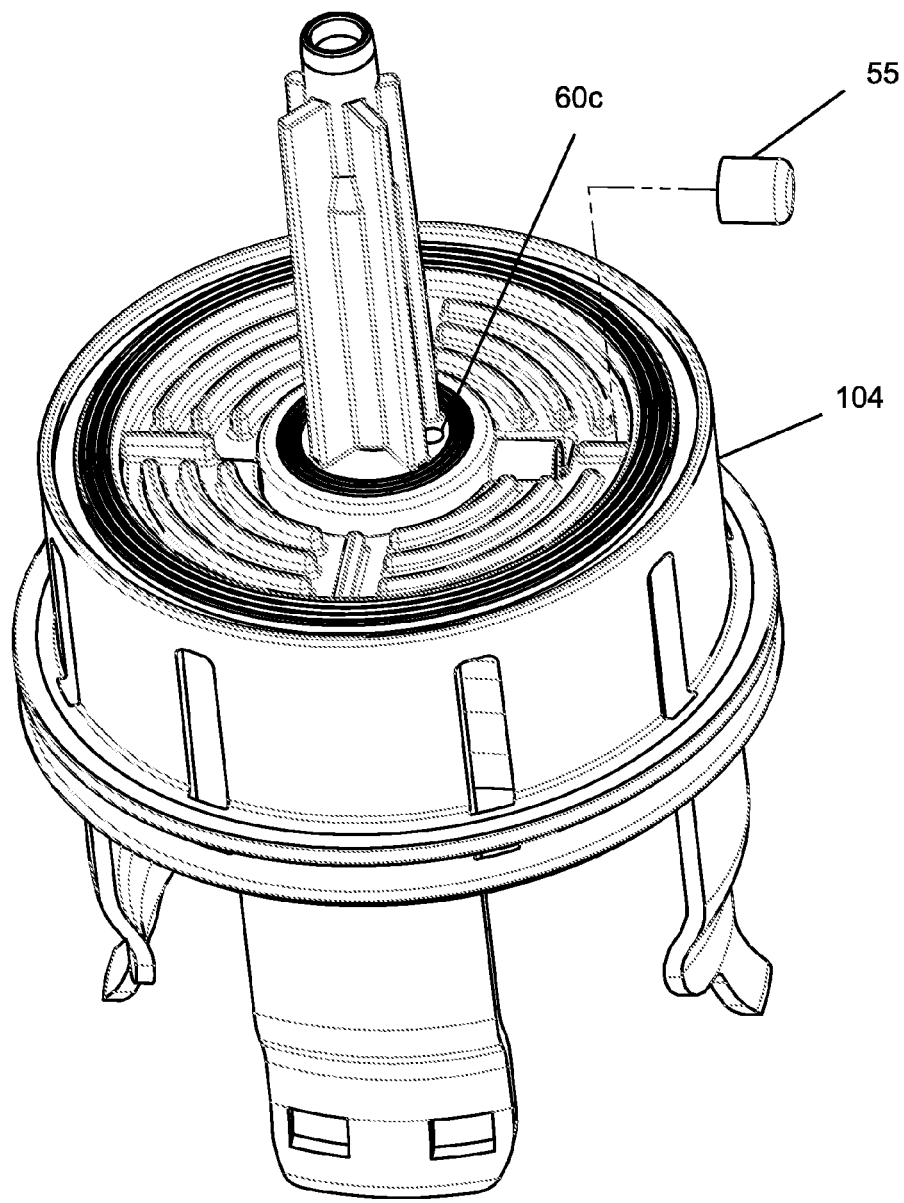

FIG. 35 shows the spike component in its place and welded to the upper part 104 of the vial adaptor. The elastic cap 55 is shown with an arrow pointing to its designated location. The upper opening 60c of flow channel C-C is visible in this figure.

Figure 36:
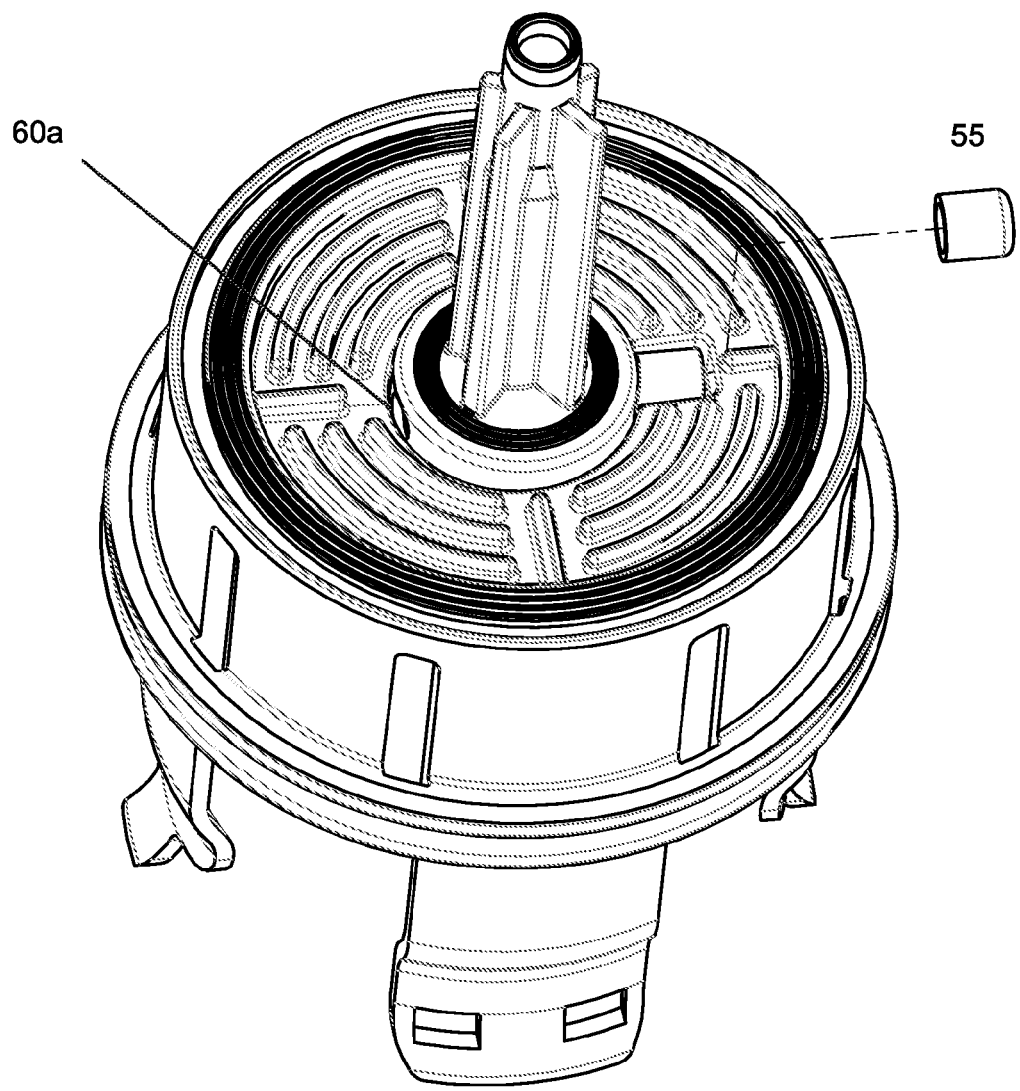

In FIG. 36 can be seen on the left side the upper opening 60a of air channel B-B.

Figure 37:
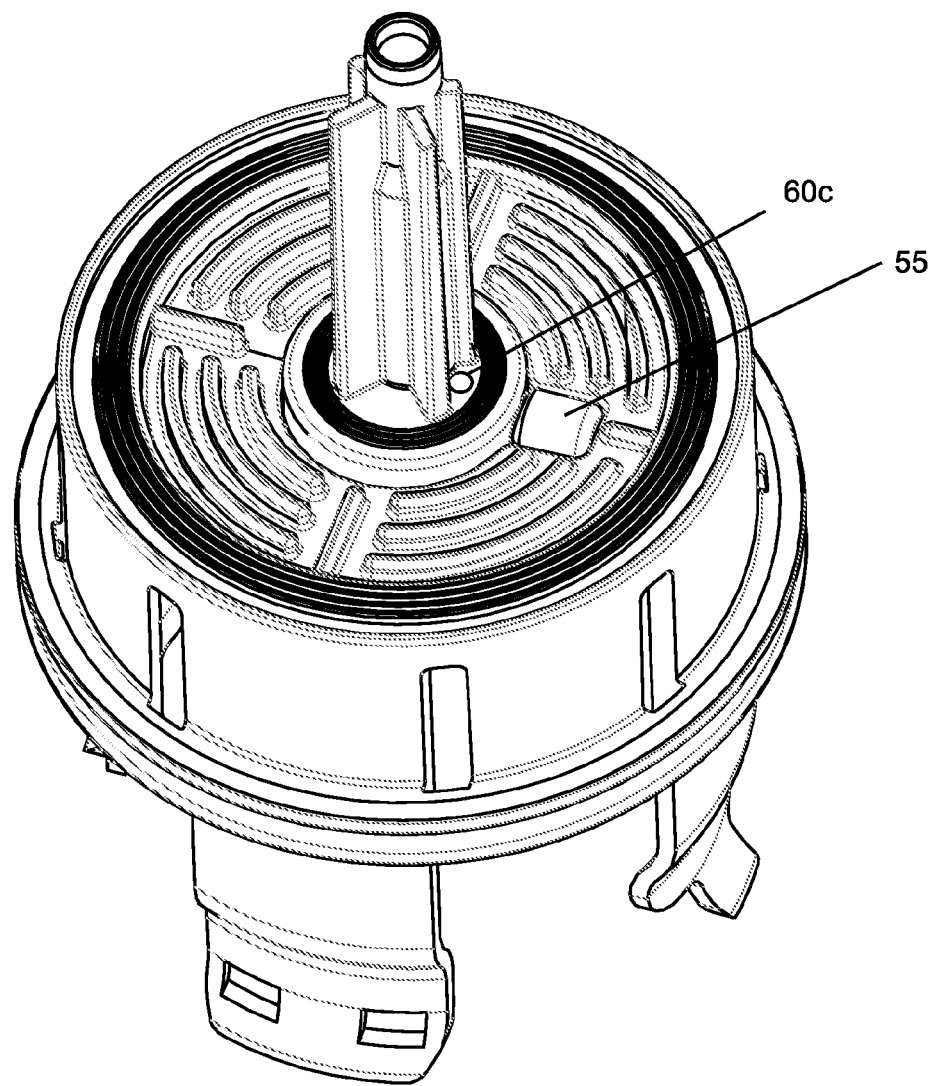

In FIG. 37 the elastic cap 55 can be seen assembled in its final location.

Figure 38:
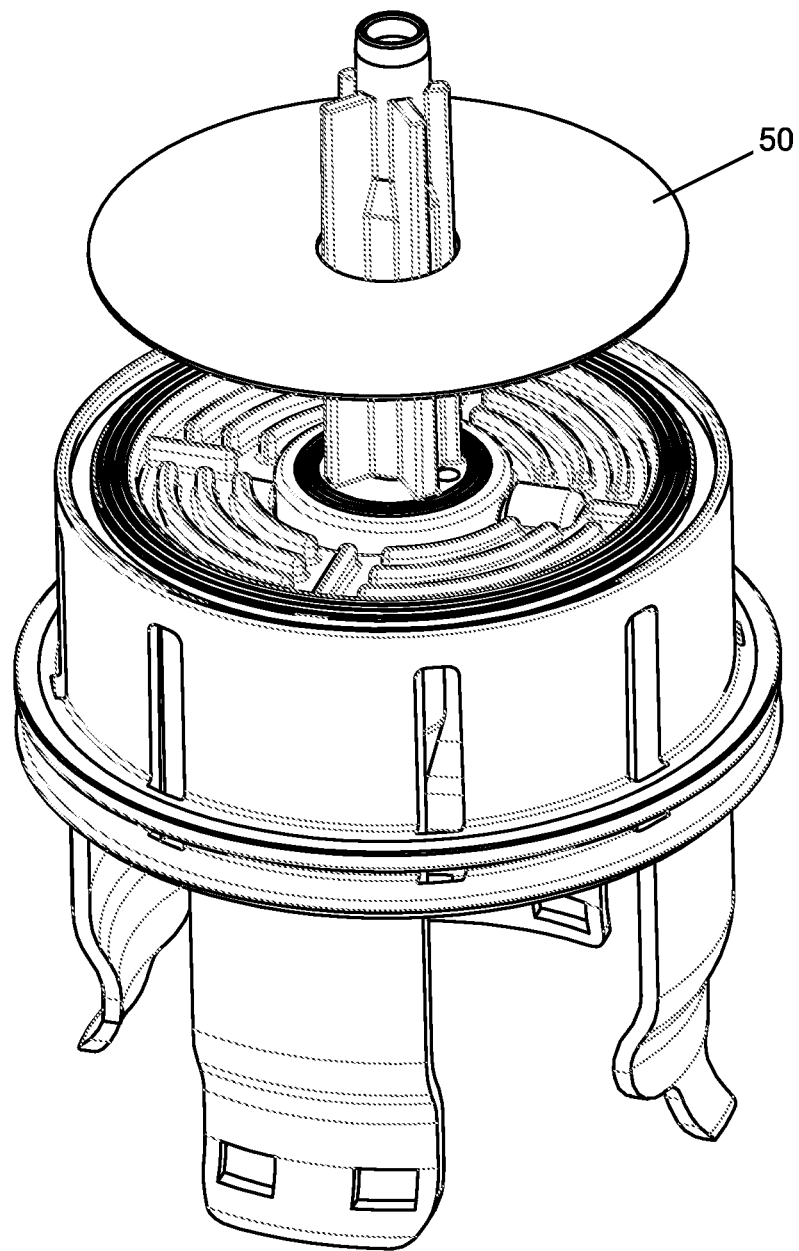

FIG. 38 shows the first step of introducing the filter disk 50 into the assembly.

Figure 39:
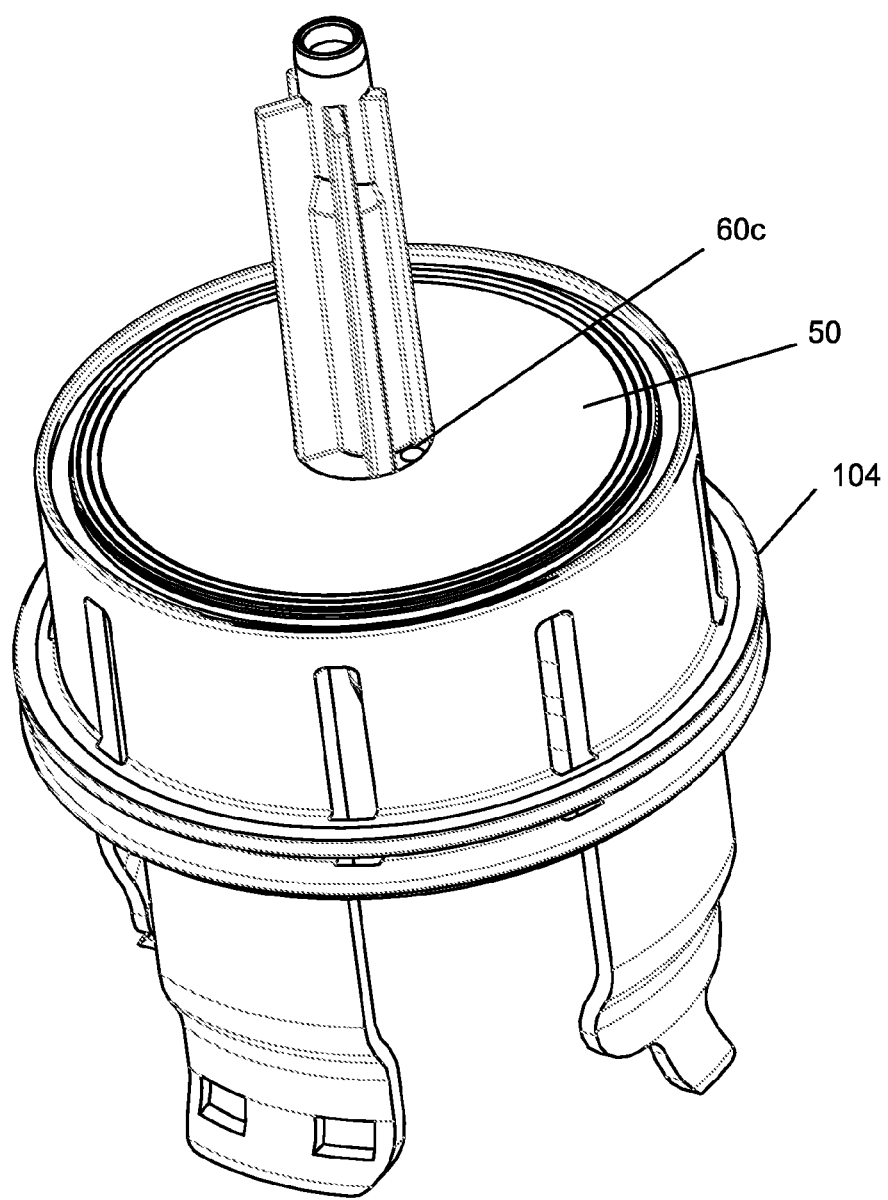

In FIG. 39 the filter is put in place and welded to the top of part 104 of the vial adaptor. Now the flow channel B-B and the elastic cap 55 are covered and isolated from the syringe by the filter 50, which serves as a barrier against liquid intrusion into the air channel C-C whose top opening 60c, as can be seen, is not covered by the filter.

Figure 40:
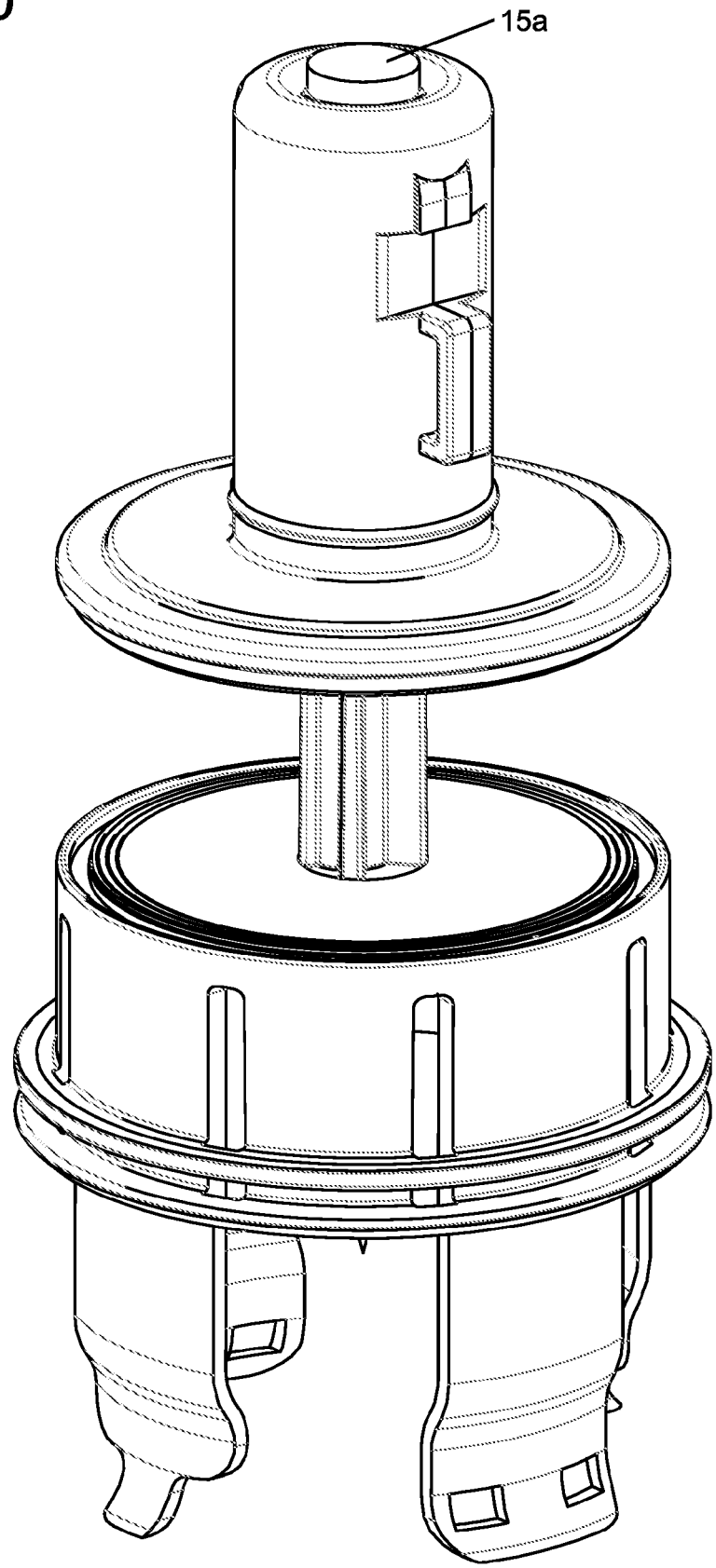

FIG. 40 shows the upper section component (see similar FIG. 13a and FIG. 13b) ready for final assembly. This component covers, seals, and encloses the top part 104 vial adaptor. Most of the interior of this component serves as air channel into the air needle 38 of the syringe is being inserted. An elastic membrane 15a seals the top of this component and serves as the access port for the syringe of this embodiment of the transfer apparatus.

Figure 41:
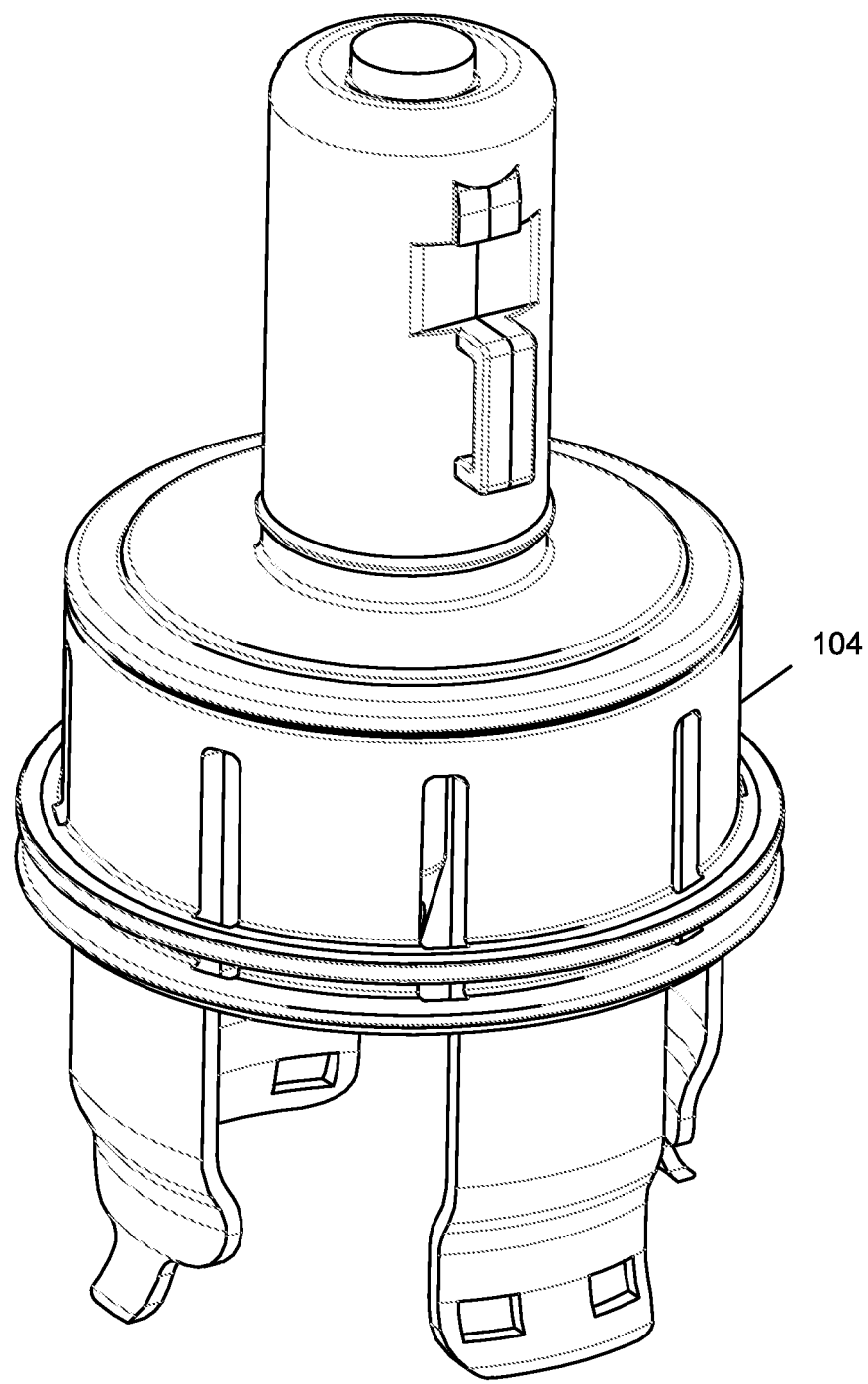

FIG. 41 shows the complete top part of the vial adaptor, sealed and ready for connection to the bottom part and then to a vial.

Protecting the Filter Against Clogging

The normal way to withdraw liquid from a vial using the fluid transfer apparatus described herein, is to invert the syringe with the vial attached to it, so that the vial is upside-down; and, the normal way to inject liquid into the vial, is to hold the vial in its upright position with the syringe above it, as can be seen in FIG. 4b and FIG. 4a respectively. If the apparatus comprises a filter in the air transfer path, then the filter requires protection against excessive pressure when the vial is in upside-down position. Normally in this position there should be no pressure on the filter, since, as the piston of the syringe is pulled downwards, air flows from the air chamber in the syringe into the vial through the filter and liquid does not enter the air channel. A problem arises when the apparatus is in this position and the operator pushes the syringe plunger in order to push an air bubble back into the vial or to push liquid back into the vial to correct the dose if too much of the liquid has been withdrawn previously. In such case pressure is created inside the vial and the liquid is forced into the vial adaptor and pressed into the filter. If the operator exaggerates and pushes too hard, then the liquid could clog the filter permanently. Therefore, when liquid is being withdrawn from the vial, as shown in FIG. 4b, it is desirable to protect the filter by closing the air channel that leads to the filter. When the vial is in upright position and liquid is injected into the vial, as shown in FIG. 4a, there is no contact between the liquid and the filter; therefore the problem of liquid clogging the filter should not arise and there is no need to protect the filter.

In order to prevent the problem of clogging of the filter described above, embodiments of the fluid transfer apparatus comprise a selective valve in the air transfer path located between the vial and the filter. When the apparatus is in the inverted position with the vial at the top, the valve must close the air path before the filter to prevent the liquid flowing in the direction of the filter from reaching it and must open the air path for normal air flow that is coming from the syringe into the vial. When the apparatus is in the upright position with the vial at the bottom, then the valve must not interfere with the flow of air in either direction.

Some different types of selective valve, e.g. solenoid valves activated by electricity or other valves activated by the pressure exerted by liquid flowing through the channels of the device, could be used. The two positions of the vial, namely upright and the inverted, suggest that a good solution would be a valve that is gravity activated. There are many ways of implementing a gravity activated selective valve in conjunction with the liquid transfer apparatus.

Figure 42A:
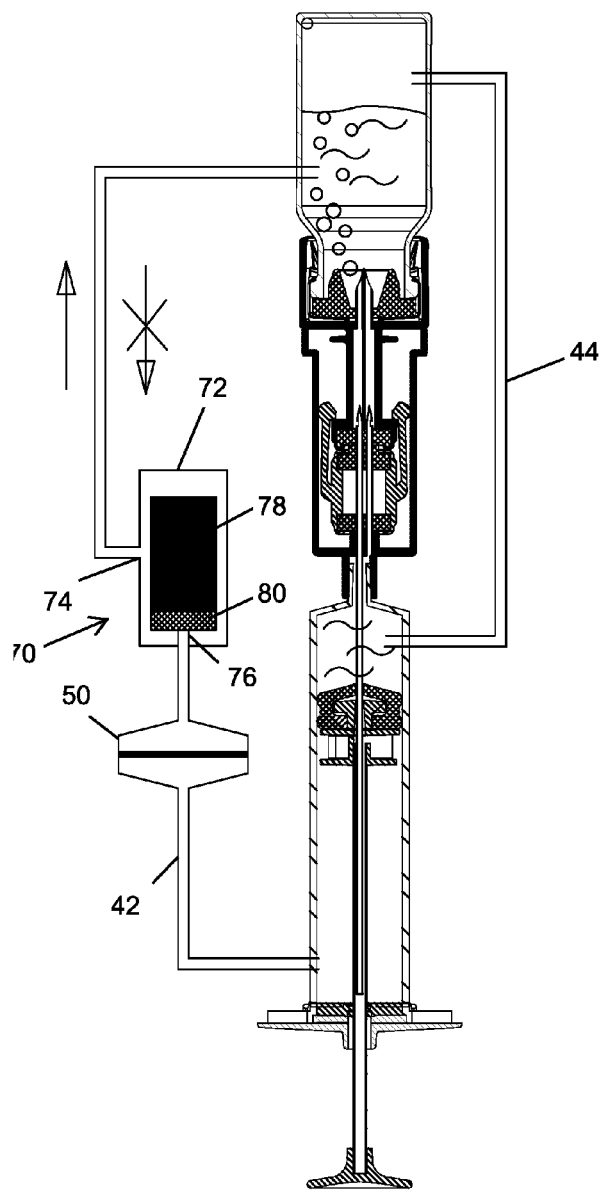
FIG. 42a and FIG. 42b schematically shown an embodiment of a gravity activated selective valve used to prevent the filter from becoming clogged.
Figure 42B:
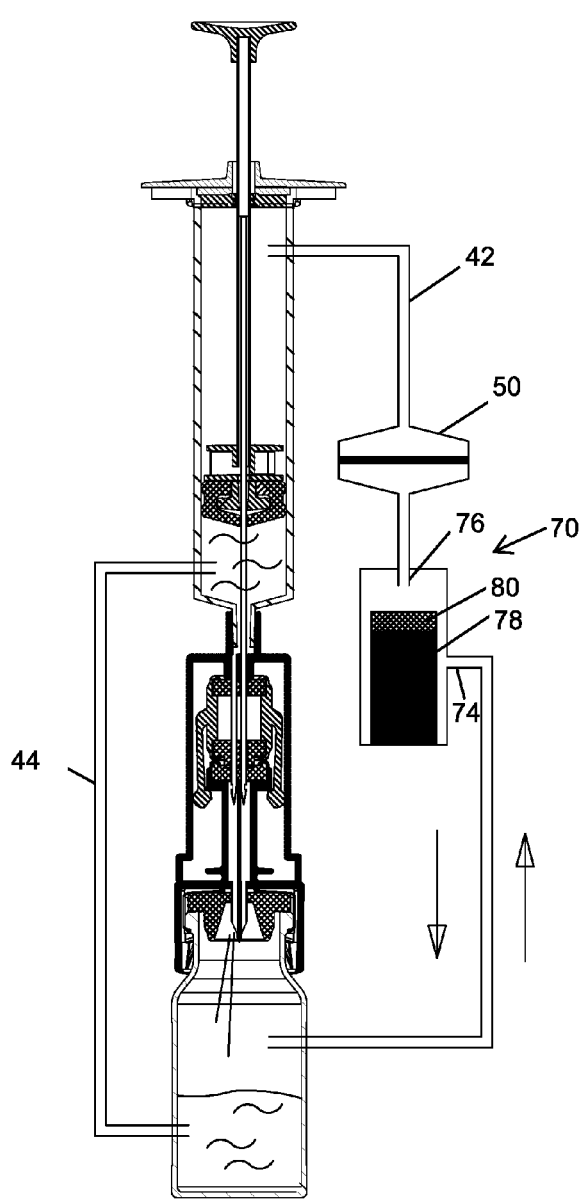

One embodiment of a gravity activated selective valve is schematically shown in FIG. 42a and FIG. 42b. These two figures are schematic and show the flow channels external to the device for clarity of presentation and convenience. In practical use the channels and components, i.e. filter and the valve are designed within or inside the device. This embodiment has been built by the inventors and found to provide the solution for protecting the filter against overpressure when placed in the air channel between the inside of the vial and the filter.

Gravity activated valves are characterized by having a heavy sealing component which can typically be displaced between two positions. In FIG. 42a with the vial in an upside-down position, the gravity activated selective valve 70 is placed in the air transfer path 42 between the vial and the filter 50. The gravity activated valve consists of housing 72 having an opening 74 on its side and another opening 76 on its proximal end. Inside of housing 72 is a heavy weight 78 with an elastic layer 80, e.g. made from silicone rubber, connected to the end of the weight that faces opening 76. The dimensions of the weight 78 and elastic layer 80 are such that the weight can move freely inside housing 72 a short distance in a direction parallel to a longitudinal axis of housing. In the position of FIG. 42a gravity pulls the weight 78 downwards pressing the elastic layer 80 onto the narrow opening 76. In this position, if liquid is pushed into the air transfer path 42, the liquid can enter housing 72 from the side through inlet 74 but cannot flow out because of the elastic layer 80 blocking opening 76. Because any liquid or air forced into the housing of the valve will assist gravity in pushing the weight 78 downward, the higher the pressure that is created in the vial the better opening 76 of the valve is sealed.

In the position shown in FIG. 42a, if air is flowing in air transfer path 42 in the opposite direction, namely from the syringe to the vial, the pressure exerted by the air lifts the weight 78 and elastic layer 80 unblocking outlet 76 allowing the air to flow unhindered through housing 72 and to continue on its way to the vial through opening 74. When the air flow stops, weight 78 falls down and elastic layer 80 again seals opening 76.

In FIG. 42*b* the vial position is now upright and the one-way valve 70 is fully open for any flow direction, namely: the heavy weight 78 with its elastic layer 80 are displaced by gravity such that both openings 76,78 in housing 72 are open.

To avoid the elastic layer 80 and attached weight 78 from sticking to opening 76 by vacuum when the apparatus is inverted, opening 76 is not created directly in the wall of housing 72 but is at the end of piece of tubing that has a very small diameter and projects a short distance into the interior of housing 72 as shown in FIGS. 42*a* and 42*b*.

The reason why the opening 74 is placed on the side of the housing 72 is to avoid the weight 78 from being displaced by the fast flowing air towards the tube opening 76 and blocking the flow. This could happen if the opening 74 would be made in the housing 72 at the opposite side of opening 76, although this is a more simpler and intuitive construction this wouldn't work in certain cases as described before, the weight 78 would be pushed onto the opening 76 by the flowing fluids and would block the flow and desired function, therefore the side entrance is the preferred method where the flow of fluids has a neutral effect on the displacement of the weight. Although the channels leading to the gravity activated valve are described schematically in FIGS. 42*a* and 42*b*, the drawing of the valve housing and valve are accurate and can be made exactly as shown in the figures.

Although embodiments of the invention have been described by way of illustration, it will be understood that the invention may be carried out with many variations, modifications, and adaptations, without exceeding the scope of the claims.

The invention claimed is:

1. A fluid transfer apparatus comprising:
    (a) a syringe-like proximal section comprising:
        (i) a cylindrical body;
        (ii) a piston that is displaceable within said cylindrical body, said piston defining a distal liquid chamber and a proximal air chamber, both of variable volume;
    (b) a connector section fixedly attached to the distal end of said proximal section, wherein the distal end of said connector section is adapted to be connectable to a fluid transfer component, said connector section comprising:
        (i) a needle holder;
        (ii) a liquid conduit that passes through and is rigidly attached to said needle holder, wherein the distal end of said liquid conduit begins in said connector section and the proximal end of said liquid conduit terminates in said distal liquid chamber;
        (iii) an air conduit that passes through and is rigidly attached to said needle holder, wherein the distal end of said air conduit begins in said connector section and the proximal end of said air conduit terminates in said proximal air chamber; and
        (iv) a membrane located at the distal end of said connector section, wherein said membrane encloses the distal ends of said liquid conduit and said air conduit isolating them from the surroundings;
    wherein, said connector section is configured to allow a head portion of said fluid transfer component to enter the interior of said connector section and to allow said membrane in said connector section to be pushed proximally when it is contacted by a membrane located in said head portion of said fluid transfer component; whereupon further pushing of said membranes together causes said distal ends of said liquid conduit and said air conduit to penetrate said membrane in said connector section and to penetrate said membrane in said head portion, thereby establishing a liquid channel via said liquid conduit between the interior of said distal liquid chamber and the interior of said fluid transfer component and a separate air channel via said air conduit between the interior of said proximal air chamber and the interior of said fluid transfer component;
    said fluid transfer apparatus characterized in that a hydrophobic filter is inserted in said air channel in at least one location between said proximal air chamber in said syringe-like proximal section of said fluid transfer apparatus and said fluid transfer component.

2. The apparatus of claim 1, wherein a section of the air channel is located outside of said apparatus.

3. The apparatus of claim 1, wherein the connector section comprises a hollow cylindrical outer body having:
    (a) a distal shoulder portion radially protruding from said outer body and terminating with an opening through which the proximal end of a fluid transfer component can be inserted for coupling;
    (b) a closed proximal cap having a central portion comprising connection means protruding proximally from it to connect to the syringe-like proximal portion of said apparatus;
    (c) a needle holder protruding into the interior of said outer body from a central portion of said closed proximal cap for retaining therein two conduits comprising sharp pointed ends and further provided with apertures through which liquid and air respectively are transferred during a fluid transfer operation; and
    (d) a double membrane seal actuator reciprocably displaceable within the hollow interior of said outer body;
    wherein said double membrane seal actuator comprises:
        (i) a cylindrical actuator casing;
        (ii) a proximal membrane that seals the proximal end of said casing
        (iii) a distal membrane that seals the distal end of said casing, wherein a part of said distal membrane protrudes distally from said casing; and
        (iv) at least one resilient arm which is connected at a proximal end thereof to an intermediate portion of the exterior of said casing and comprises an enlarged locking element at its distal end; said enlarged locking element having specifically shaped surface areas which interact with the inner wall of said hollow cylindrical outer body of said connector section to enable a four step procedure for connecting or separating said connector section to a fluid transfer component.

4. The apparatus of claim 3, comprising a sleeve made of an elastic material, said sleeve surrounding the tip and the distal opening of the needle of the air conduit inside the double membrane seal actuator.

5. The apparatus of claim 1, wherein the connector section comprises a hollow cylindrical outer body having:
    (a) a distal shoulder portion radially protruding from said outer body and terminating with an opening through which the proximal end of a fluid transfer component can be inserted for coupling;
    (b) a closed proximal cap having a central portion comprising connection means protruding proximally from it to connect to the throat of the syringe-like proximal portion of said apparatus;
    (c) an elongated cylindrical needle holder protruding into the interior of said outer body from a central portion of said closed proximal cap for retaining therein two conduits comprising sharp pointed ends and further provided with apertures through which liquid and air respectively are transferred during a fluid transfer operation; and (d) a single membrane seal actuator reciprocably displaceable within the hollow interior of said outer body;

wherein said single membrane seal actuator comprises:

(i) a cylindrical actuator casing;

(ii) a proximal O-ring that seals the proximal end of said casing to the outer surface of said elongated cylindrical needle holder;

(iii) a distal membrane that seals the distal end of said casing, wherein a part of said distal membrane protrudes distally from said casing; and (iv) at least one resilient arm which is connected at a proximal end thereof to an intermediate portion of the exterior of said casing and comprises enlarged locking elements at its distal end; said enlarged locking element having specifically shaped surface areas which interact with the inner wall of said hollow cylindrical outer body of said connector section to enable a four step procedure for connecting or separating said connector section to a fluid transfer component.

6. The apparatus of claim 5, comprising a sleeve made of an elastic material, said sleeve surrounding the tip and the distal opening of the needle of the air conduit inside the single membrane seal actuator.

7. The apparatus of claim 1, wherein the fluid transfer component is a vial adaptor, wherein said vial adaptor comprises an air channel and a separate liquid channel, thereby providing a closed transfer system that does not vent to or communicate with the environment.

8. The apparatus of claim 7, wherein the vial adaptor comprises:

(a) a distal collar portion comprised of a disk shaped central piece with a plurality of segments adapted for facilitating securement of said vial adaptor to a head portion of a medical vial or any type of vessel or device that has a head section similar to that of the head portion of a standard medicine vial, said segments attached to the circumference of said disk shaped central piece and projecting distally away from it;

(b) a longitudinal extension projecting proximally from said disk shaped central piece said longitudinal extension adapted to be coupled to a fluid transfer device;

(c) a membrane that seals the proximal end of said longitudinal extension;

(d) a spike element which protrudes distally from the center of said disk shaped central piece;

(e) an air channel and a liquid channel both of which are internally formed within said longitudinal extension and said spike element, said channels adapted to allow fluid communication through said vial adapter from said proximally located membrane to openings at the tip of said spike;

wherein an annular shaped flat hydrophobic filter is located in said disk shaped central piece, said vial adaptor and said filter adapted to allow fluid flowing in said liquid channel to pass through said vial adapter without passing through said filter and to force fluid flowing through said air channel to pass through said filter.

9. The apparatus of claim 8, wherein one or both of the outer and inner circumferential edges of the annular shaped flat hydrophobic filter are welded, glued, or mechanically pressed to the vial adaptor.

10. The apparatus of claim 8, wherein the annular shaped flat hydrophobic filter is supported by and lays on plurality of closely spaced supporting ribs from one or both of above and below.

11. The apparatus of claim 8, comprising a by-pass comprising a one-way valve placed in parallel to the filter in the air channel.

12. The apparatus of claim 11, wherein the one-way valve is comprised of an elastic cap, which is tightly fit over an end of a rigid tube.

13. The apparatus of claim 7, wherein the vial adaptor comprises:

(a) a bottom part adapted to be attached to the head section of a medical vial or any type of vessel or device that has a head section similar to that of the head of a standard medicine vial;

(b) a top part comprising:

(i) a disk shaped central piece and a plurality of wings adapted for facilitating securement of said top part to said bottom part, said wings attached to the circumference of said disk shaped central piece and projecting distally away from it;

(ii) a longitudinal extension projecting proximally from said disk shaped central piece, said longitudinal extension adapted to be coupled to a fluid transfer device;

(iii) a membrane that seals the proximal end of said longitudinal extension;

(iv) a spike element which protrudes distally from the center of said disk shaped central piece;

(v) an air channel and a liquid channel both of which are internally formed within said longitudinal extension and said spike element, said channels adapted to allow fluid communication through said vial adapter from said proximally located membrane to openings at the tip of said spike;

(c) a first locking mechanism; and (d) a second locking mechanism;

wherein, said first locking mechanism is adapted to lock said top part to said bottom part such that the tip of said spike cannot contact a stopper in said head section when said head section is being attached to said bottom part and to release said top part from said bottom part after said bottom part has been attached to said head section; and said second locking mechanism is adapted to allow, after said bottom part has been attached to said head section, said spike to penetrate said stopper in said head section and to irremovably lock said top part to said bottom part.

14. The apparatus of claim 13, wherein an annular shaped flat hydrophobic filter is located in said disk shaped element, said vial adaptor and said filter adapted to allow fluid flowing in said liquid channel to pass through said vial adapter without passing through said filter and to force fluid flowing through said air channel to pass through said filter.

15. The apparatus of claim 1, comprising a selective valve in the air path located between the filter and the fluid transfer component to which or from which liquid is being transferred.

16. The apparatus of claim 15, wherein said selective valve is activated by one of: electricity, pressure, or gravity.

17. The apparatus of claim 16, wherein the selective valve is a gravity activated valve comprising a housing having a first opening on its side and a second opening on its end, a heavy weight inside of said housing, and an elastic layer connected to the end of said weight that faces said second opening; wherein the dimensions of said weight and said elastic layer are such that said weight can move freely inside housing a short distance in a direction parallel to a longitudinal axis of housing; wherein in a first vertical orientation gravity pulls said weight downwards pressing said elastic layer onto said second opening, thereby preventing fluid from entering said housing through said second opening; and wherein an inverted vertical orientation gravity pulls said weight and attached elastic layer away from said second housing, thereby allowing fluid to enter said housing through said second opening.

* * * * *